(12) United States Patent
Hochman et al.

(10) Patent No.: US 9,089,382 B2
(45) Date of Patent: Jul. 28, 2015

(54) METHOD AND APPARATUS FOR RECORDING SPATIAL GINGIVAL SOFT TISSUE RELATIONSHIP TO IMPLANT PLACEMENT WITHIN ALVEOLAR BONE FOR IMMEDIATE-IMPLANT PLACEMENT

(71) Applicant: Biomet 3i LLC, Palm Beach Gardens, FL (US)

(72) Inventors: Mark N. Hochman, Great Neck, NY (US); Stephen J. Chu, New York, NY (US); Jocelyn Huiping Tan-Chu, New York, NY (US); Adam J. Mieleszko, Arverne, NY (US)

(73) Assignee: Biomet 3i, LLC, Palm Beach Gardens, FL (US)

( * ) Notice: Subject to any disclaimer, the term of this patent is extended or adjusted under 35 U.S.C. 154(b) by 105 days.

(21) Appl. No.: 13/655,056

(22) Filed: Oct. 18, 2012

(65) Prior Publication Data

US 2013/0189646 A1     Jul. 25, 2013

Related U.S. Application Data

(63) Continuation-in-part of application No. 13/356,359, filed on Jan. 23, 2012, now Pat. No. 8,425,231.

(51) Int. Cl.
*A61C 8/00*     (2006.01)
*A61C 9/00*     (2006.01)
(Continued)

(52) U.S. Cl.
CPC ............ *A61C 8/0077* (2013.01); *A61C 8/0001* (2013.01); *A61C 9/004* (2013.01); *A61C 13/0001* (2013.01); *A61C 13/0004* (2013.01)

(58) Field of Classification Search
CPC ...... A61C 8/00; A61C 8/0004; A61C 8/0037; A61C 8/004; A61C 8/0054; A61C 8/0053; A61C 8/0077
USPC ........................................ 433/172–176, 201.1
See application file for complete search history.

(56) References Cited

U.S. PATENT DOCUMENTS 3,906,634 A    9/1975  Aspel
3,919,772 A    11/1975 Lenczycki
(Continued)

FOREIGN PATENT DOCUMENTS

DE           10029256        11/2000
WO        WO 94/26200        11/1994
(Continued)

OTHER PUBLICATIONS

Biomet 3i—Manual entitled "Navigator™ System For CT Guided Surgery Manual", Revision A Oct. 2007—34 pages.
(Continued)

*Primary Examiner* — Yogesh Patel
(74) *Attorney, Agent, or Firm* — Nixon & Peabody LLP

(57) ABSTRACT

A dental implant has a hollow shell with outer bio-compatible surface for engaging a soft tissue socket left in gingival tissue after a tooth has been extracted, to promote healing. The shell tapers outwardly from a first to a second perimeter, the second perimeter being asymmetrically scalloped with opposite distal and mesial peaks and opposite lingual and facial valleys between the peaks. A dental implant in the bone socket left after tooth extraction is rigidly connected to a temporary post, the temporary post extending in the shell. The shell engages against the soft tissue socket without gaps and without requiring alignment between the shell and implant axes.

19 Claims, 14 Drawing Sheets

(51) Int. Cl.
*A61C 13/107* (2006.01)
*A61C 13/00* (2006.01)

(56) References Cited

U.S. PATENT DOCUMENTS

| | | | |
|---|---|---|---|
| 3,958,471 A | 5/1976 | Muller | |
| 4,011,602 A | 3/1977 | Rybicki et al. | |
| 4,056,585 A | 11/1977 | Waltke | |
| 4,086,701 A | 5/1978 | Kawahara et al. | |
| 4,177,562 A | 12/1979 | Miller et al. | |
| 4,294,544 A | 10/1981 | Altschuler et al. | |
| 4,306,862 A | 12/1981 | Knox | |
| 4,325,373 A | 4/1982 | Slivenko et al. | |
| 4,341,312 A | 7/1982 | Scholer | |
| 4,364,381 A | 12/1982 | Sher et al. | |
| 4,439,152 A | 3/1984 | Small | |
| 4,543,953 A | 10/1985 | Slocum et al. | |
| 4,547,157 A | 10/1985 | Driskell | |
| 4,571,180 A | 2/1986 | Kulick | |
| 4,611,288 A | 9/1986 | Duret et al. | |
| 4,624,673 A | 11/1986 | Meyer | |
| 4,663,720 A | 5/1987 | Duret et al. | |
| 4,713,004 A | 12/1987 | Linkow et al. | |
| 4,756,689 A | 7/1988 | Lundgren | |
| 4,758,161 A | 7/1988 | Niznick | |
| 4,767,331 A | 8/1988 | Hoe | |
| 4,772,204 A | 9/1988 | Soderberg | |
| 4,821,200 A | 4/1989 | Öberg | |
| 4,842,518 A | 6/1989 | Linkow et al. | |
| 4,850,870 A | 7/1989 | Lazzara et al. | |
| 4,850,873 A | 7/1989 | Lazzara et al. | |
| 4,854,872 A | 8/1989 | Detsch | |
| 4,856,994 A | 8/1989 | Lazzara et al. | |
| 4,872,839 A | 10/1989 | Brajnovic | |
| 4,906,191 A | 3/1990 | Soderberg | |
| 4,906,420 A | 3/1990 | Brajnovic | |
| 4,931,016 A | 6/1990 | Sillard | |
| 4,935,635 A | 6/1990 | O'Harra | |
| 4,961,674 A | 10/1990 | Wang et al. | |
| 4,964,770 A | 10/1990 | Steinbichler et al. | |
| 4,986,753 A | 1/1991 | Sellers | |
| 4,988,297 A | 1/1991 | Lazzara et al. | |
| 4,988,298 A | 1/1991 | Lazzara et al. | |
| 4,998,881 A | 3/1991 | Lauks | |
| 5,000,685 A | 3/1991 | Brajnovic | |
| 5,006,069 A | 4/1991 | Lazzara et al. | |
| 5,015,183 A | 5/1991 | Fenick | |
| 5,015,186 A | 5/1991 | Detsch | |
| 5,030,096 A | 7/1991 | Hurson et al. | |
| 5,035,619 A | 7/1991 | Daftary | |
| 5,040,982 A | 8/1991 | Stefan-Dogar | |
| 5,040,983 A | 8/1991 | Binon | |
| 5,064,375 A | 11/1991 | Jörnéus | |
| 5,071,351 A | 12/1991 | Green, Jr. et al. | |
| 5,073,111 A | 12/1991 | Daftary | |
| 5,087,200 A | 2/1992 | Brajnovic et al. | |
| 5,100,323 A | 3/1992 | Friedman et al. | |
| 5,104,318 A | 4/1992 | Piche et al. | |
| 5,106,300 A | 4/1992 | Voitik | |
| 5,122,059 A | 6/1992 | Durr et al. | |
| 5,125,839 A | 6/1992 | Ingber et al. | |
| 5,125,841 A | 6/1992 | Carlsson et al. | |
| 5,133,660 A | 7/1992 | Fenick | |
| 5,135,395 A | 8/1992 | Marlin | |
| 5,145,371 A | 9/1992 | Jörnéus | |
| 5,145,372 A | 9/1992 | Daftary et al. | |
| 5,176,516 A | 1/1993 | Koizumi | |
| 5,188,800 A | 2/1993 | Green, Jr. et al. | |
| 5,195,892 A | 3/1993 | Gersberg | |
| 5,205,745 A | 4/1993 | Kamiya et al. | |
| 5,209,659 A | 5/1993 | Friedman et al. | |
| 5,209,666 A | 5/1993 | Balfour et al. | |
| 5,213,502 A | 5/1993 | Daftary | |
| 5,221,204 A | 6/1993 | Kruger et al. | |
| 5,237,998 A | 8/1993 | Duret et al. | |
| 5,246,370 A | 9/1993 | Coatoam | |
| 5,257,184 A | 10/1993 | Mushabac | |
| 5,281,140 A | 1/1994 | Niznick | |
| 5,286,195 A | 2/1994 | Clostermann | |
| 5,286,196 A | 2/1994 | Brajnovic et al. | |
| 5,292,252 A | 3/1994 | Nickerson et al. | |
| 5,297,963 A | 3/1994 | Dafatry | |
| 5,302,125 A | 4/1994 | Kownacki et al. | |
| 5,312,254 A | 5/1994 | Rosenlicht | |
| 5,312,409 A | 5/1994 | McLaughlin et al. | |
| 5,316,476 A | 5/1994 | Krauser | |
| 5,320,529 A | 6/1994 | Pompa | |
| 5,328,371 A | 7/1994 | Hund et al. | |
| 5,334,024 A | 8/1994 | Niznick | |
| 5,336,090 A | 8/1994 | Wilson, Jr. et al. | |
| 5,338,196 A | 8/1994 | Beaty et al. | |
| 5,338,198 A | 8/1994 | Wu et al. | |
| 5,343,391 A | 8/1994 | Mushabac | |
| 5,344,457 A | 9/1994 | Pilliar et al. | |
| 5,350,297 A | 9/1994 | Cohen | |
| 5,359,511 A | 10/1994 | Schroeder et al. | |
| 5,362,234 A | 11/1994 | Salazar et al. | |
| 5,362,235 A | 11/1994 | Daftary | |
| 5,368,483 A | 11/1994 | Sutter et al. | |
| 5,370,692 A | 12/1994 | Fink | |
| 5,372,502 A | 12/1994 | Massen et al. | |
| 5,386,292 A | 1/1995 | Massen et al. | |
| 5,413,481 A | 5/1995 | Göppel et al. | |
| 5,417,568 A * | 5/1995 | Giglio | 433/173 |
| 5,417,569 A | 5/1995 | Perisse | |
| 5,417,570 A | 5/1995 | Zuest et al. | |
| 5,419,702 A | 5/1995 | Beaty et al. | |
| 5,431,567 A | 7/1995 | Datary | |
| 5,437,551 A | 8/1995 | Chalifoux | |
| 5,440,393 A | 8/1995 | Wenz | |
| 5,452,219 A | 9/1995 | Dehoff et al. | |
| 5,458,488 A | 10/1995 | Chalifoux | |
| 5,476,382 A | 12/1995 | Daftary | |
| 5,476,383 A | 12/1995 | Beaty et al. | |
| 5,492,471 A | 2/1996 | Singer | |
| 5,516,288 A | 5/1996 | Sichler et al. | |
| 5,527,182 A | 6/1996 | Willoughby | |
| 5,533,898 A | 7/1996 | Mena | |
| 5,538,426 A | 7/1996 | Harding et al. | |
| 5,547,377 A | 8/1996 | Daftary | |
| 5,556,278 A | 9/1996 | Meitner | |
| 5,564,921 A | 10/1996 | Marlin | |
| 5,564,924 A | 10/1996 | Kwan | |
| 5,569,578 A | 10/1996 | Mushabac | |
| 5,571,016 A | 11/1996 | Ingber et al. | |
| 5,575,656 A | 11/1996 | Hajjar | |
| 5,580,244 A | 12/1996 | White | |
| 5,580,246 A | 12/1996 | Fried | |
| 5,595,703 A | 1/1997 | Swaelens et al. | |
| 5,613,832 A | 3/1997 | Su | |
| 5,613,852 A | 3/1997 | Bavitz | |
| 5,630,717 A | 5/1997 | Zuest | |
| 5,636,986 A | 6/1997 | Pezeshkian | |
| 5,651,675 A | 7/1997 | Singer | |
| 5,652,709 A | 7/1997 | Andersson et al. | |
| 5,658,147 A | 8/1997 | Phimmasone | |
| 5,662,476 A | 9/1997 | Ingber et al. | |
| 5,674,069 A | 10/1997 | Osorio | |
| 5,674,071 A | 10/1997 | Beaty et al. | |
| 5,674,073 A | 10/1997 | Ingber et al. | |
| 5,681,167 A | 10/1997 | Lazarof | |
| 5,685,715 A | 11/1997 | Beaty et al. | |
| 5,688,283 A | 11/1997 | Knapp | |
| 5,704,936 A | 1/1998 | Mazel | |
| 5,718,579 A | 2/1998 | Kennedy | |
| 5,725,376 A | 3/1998 | Poirier | |
| 5,733,124 A | 3/1998 | Kwan | |
| 5,741,215 A | 4/1998 | D'Urso | |
| 5,743,916 A | 4/1998 | Greenberg | |
| 5,759,036 A | 6/1998 | Hinds | |
| 5,762,125 A | 6/1998 | Mastrorio | |
| 5,762,500 A | 6/1998 | Lazarof | |
| 5,768,134 A | 6/1998 | Swaelens et al. | |
| 5,769,636 A | 6/1998 | Di Sario | |

(56) References Cited

U.S. PATENT DOCUMENTS

| | | |
|---|---|---|
| 5,791,902 A | 8/1998 | Lauks |
| 5,800,168 A | 9/1998 | Cascione et al. |
| 5,813,858 A | 9/1998 | Singer |
| 5,823,778 A | 10/1998 | Schmitt et al. |
| 5,842,859 A | 12/1998 | Palacci |
| 5,846,079 A | 12/1998 | Knode |
| 5,851,115 A | 12/1998 | Carlsson et al. |
| 5,857,853 A | 1/1999 | Van Nifterick et al. |
| 5,871,358 A | 2/1999 | Ingber et al. |
| 5,873,722 A | 2/1999 | Lazzara et al. |
| 5,876,204 A | 3/1999 | Day et al. |
| 5,885,078 A | 3/1999 | Cagna et al. |
| 5,888,034 A | 3/1999 | Greenberg |
| 5,899,695 A | 5/1999 | Lazzara et al. |
| 5,899,697 A | 5/1999 | Lazzara et al. |
| 5,904,483 A | 5/1999 | Wade |
| 5,915,962 A | 6/1999 | Rosenlicht |
| 5,927,982 A | 7/1999 | Kruger |
| 5,931,675 A | 8/1999 | Callan |
| 5,938,443 A | 8/1999 | Lazzara et al. |
| 5,954,769 A | 9/1999 | Rosenlicht |
| 5,964,591 A | 10/1999 | Beaty et al. |
| 5,967,777 A | 10/1999 | Klein et al. |
| 5,984,681 A | 11/1999 | Huang |
| 5,989,025 A | 11/1999 | Conley |
| 5,989,029 A | 11/1999 | Osorio |
| 5,989,258 A | 11/1999 | Hattori |
| 5,997,681 A | 12/1999 | Kinzie |
| 6,000,939 A | 12/1999 | Ray et al. |
| 6,008,905 A | 12/1999 | Breton et al. |
| 6,030,219 A | 2/2000 | Zuest et al. |
| 6,068,479 A | 5/2000 | Kwan |
| 6,099,311 A | 8/2000 | Wagner et al. |
| 6,099,313 A | 8/2000 | Dorken et al. |
| 6,099,314 A | 8/2000 | Kopelman et al. |
| 6,120,293 A | 9/2000 | Lazzara et al. |
| 6,129,548 A | 10/2000 | Lazzara et al. |
| 6,135,773 A | 10/2000 | Lazzara |
| 6,142,782 A | 11/2000 | Lazarof |
| 6,174,168 B1 | 1/2001 | Dehoff et al. |
| 6,175,413 B1 | 1/2001 | Lucas |
| 6,190,169 B1 | 2/2001 | Bluemli et al. |
| 6,197,410 B1 | 3/2001 | Vallittu et al. |
| 6,200,125 B1 | 3/2001 | Akutagawa |
| 6,206,693 B1 | 3/2001 | Hultgren |
| 6,210,162 B1 | 4/2001 | Chishti |
| 6,217,334 B1 | 4/2001 | Hultgren |
| 6,227,857 B1 | 5/2001 | Morgan et al. |
| 6,227,859 B1 | 5/2001 | Sutter |
| 6,283,753 B1 | 9/2001 | Willoughby |
| 6,287,119 B1 | 9/2001 | van Nifterick |
| 6,296,483 B1 | 10/2001 | Champleboux |
| 6,305,939 B1 | 10/2001 | Dawood |
| 6,319,000 B1 | 11/2001 | Branemark |
| 6,322,728 B1 | 11/2001 | Brodkin |
| 6,382,975 B1 | 5/2002 | Poirier |
| 6,402,707 B1 | 6/2002 | Ernst |
| 6,431,866 B2 | 8/2002 | Hurson |
| 6,431,867 B1 | 8/2002 | Gittelson et al. |
| 6,488,503 B1 | 12/2002 | Lichkus et al. |
| 6,497,574 B1 | 12/2002 | Miller |
| 6,540,784 B2 | 4/2003 | Barlow |
| 6,558,162 B1 | 5/2003 | Porter et al. |
| 6,568,936 B2 | 5/2003 | MacDougald |
| 6,575,751 B1 | 6/2003 | Lehmann et al. |
| 6,594,539 B1 | 7/2003 | Geng |
| 6,610,079 B1 | 8/2003 | Li |
| 6,619,958 B2 | 9/2003 | Beaty et al. |
| 6,629,840 B2 | 10/2003 | Chishti |
| 6,634,883 B2 | 10/2003 | Ranalli |
| 6,644,970 B1 | 11/2003 | Lin |
| 6,648,640 B2 | 11/2003 | Rubbert et al. |
| 6,663,388 B1 | 12/2003 | Schar et al. |
| 6,671,539 B2 | 12/2003 | Gateno et al. |
| 6,672,870 B2 | 1/2004 | Knapp |
| 6,688,887 B2 | 2/2004 | Morgan |
| 6,691,764 B2 | 2/2004 | Embert |
| 6,743,491 B2 | 6/2004 | Cirincione et al. |
| 6,755,652 B2 | 6/2004 | Nanni |
| 6,772,026 B2 | 8/2004 | Bradbury |
| 6,776,614 B2 | 8/2004 | Wiechmann et al. |
| 6,783,359 B2 | 8/2004 | Kapit |
| 6,790,040 B2 | 9/2004 | Amber et al. |
| 6,793,491 B2 | 9/2004 | Klein et al. |
| 6,808,659 B2 | 10/2004 | Schulman |
| 6,814,575 B2 | 11/2004 | Poirier |
| 6,821,462 B2 | 11/2004 | Schulamn et al. |
| 6,829,498 B2 | 12/2004 | Kipke et al. |
| D503,804 S | 4/2005 | Phleps et al. |
| 6,882,894 B2 | 4/2005 | Durbin et al. |
| 6,885,464 B1 | 4/2005 | Pfeiffer et al. |
| 6,902,401 B2 | 6/2005 | Jorneus et al. |
| 6,913,463 B2 | 7/2005 | Blacklock |
| 6,926,442 B2 | 8/2005 | Stöckl |
| 6,926,525 B1 | 8/2005 | Ronvig |
| 6,939,489 B2 | 9/2005 | Moszner et al. |
| 6,942,699 B2 | 9/2005 | Stone et al. |
| 6,953,383 B2 | 10/2005 | Rothenberger |
| 6,957,118 B2 | 10/2005 | Kopelman et al. |
| 6,966,772 B2 | 11/2005 | Malin et al. |
| 6,970,760 B2 | 11/2005 | Wolf et al. |
| 6,971,877 B2 | 12/2005 | Harter |
| 6,994,549 B2 | 2/2006 | Brodkin et al. |
| 7,010,150 B1 | 3/2006 | Pfeiffer et al. |
| 7,010,153 B2 | 3/2006 | Zimmermann |
| 7,012,988 B2 | 3/2006 | Adler et al. |
| 7,018,207 B2 | 3/2006 | Prestipino |
| 7,021,934 B2 | 4/2006 | Aravena |
| 7,029,275 B2 | 4/2006 | Rubbert et al. |
| 7,044,735 B2 | 5/2006 | Malin |
| 7,056,115 B2 | 6/2006 | Phan et al. |
| 7,056,117 B2 * | 6/2006 | Simmons, Jr. ............... 433/173 |
| 7,056,472 B1 | 6/2006 | Behringer |
| 7,059,856 B2 | 6/2006 | Marotta |
| 7,066,736 B2 | 6/2006 | Kumar et al. |
| 7,084,868 B2 | 8/2006 | Farag et al. |
| 7,086,860 B2 | 8/2006 | Schuman et al. |
| 7,097,451 B2 | 8/2006 | Tang |
| 7,104,795 B2 | 9/2006 | Dadi |
| 7,110,844 B2 | 9/2006 | Kopelman |
| 7,112,065 B2 | 9/2006 | Kopelman |
| 7,118,375 B2 | 10/2006 | Durbin et al. |
| D532,991 S | 12/2006 | Gozzi |
| 7,153,132 B2 | 12/2006 | Tedesco |
| 7,153,135 B1 | 12/2006 | Thomas |
| 7,163,443 B2 | 1/2007 | Basler et al. |
| 7,175,434 B2 | 2/2007 | Brajnovic |
| 7,175,435 B2 | 2/2007 | Andersson et al. |
| 7,178,731 B2 | 2/2007 | Basler |
| 7,214,062 B2 | 5/2007 | Morgan |
| 7,220,124 B2 | 5/2007 | Taub et al. |
| 7,228,191 B2 | 6/2007 | Hofmeister et al. |
| 7,236,842 B2 | 6/2007 | Kopelman et al. |
| 7,281,927 B2 | 10/2007 | Marotta |
| 7,286,954 B2 | 10/2007 | Kopelman et al. |
| 7,303,420 B2 | 12/2007 | Huch et al. |
| 7,319,529 B2 | 1/2008 | Babayoff |
| 7,322,746 B2 | 1/2008 | Beckhaus et al. |
| 7,322,824 B2 | 1/2008 | Schmitt |
| 7,324,680 B2 | 1/2008 | Zimmermann |
| 7,329,122 B1 | 2/2008 | Scott |
| 7,333,874 B2 | 2/2008 | Taub et al. |
| 7,335,876 B2 | 2/2008 | Eiff et al. |
| D565,184 S | 3/2008 | Royzen |
| 7,367,801 B2 | 5/2008 | Saliger |
| 7,379,584 B2 | 5/2008 | Rubbert et al. |
| D571,471 S | 6/2008 | Stöckl |
| 7,381,191 B2 | 6/2008 | Fallah |
| 7,383,094 B2 | 6/2008 | Kopelman et al. |
| D575,747 S | 8/2008 | Abramovich et al. |
| 7,421,608 B2 | 9/2008 | Schron |
| 7,425,131 B2 | 9/2008 | Amber et al. |
| 7,429,175 B2 | 9/2008 | Gittelson |
| 7,435,088 B2 | 10/2008 | Brajnovic |

(56) References Cited

U.S. PATENT DOCUMENTS

| | | |
|---|---|---|
| 7,476,100 B2 | 1/2009 | Kuo |
| 7,481,647 B2 | 1/2009 | Sambu et al. |
| 7,488,174 B2 | 2/2009 | Kopelman et al. |
| 7,497,619 B2 | 3/2009 | Stoeckl |
| 7,497,983 B2 | 3/2009 | Khan et al. |
| 7,520,747 B2 | 4/2009 | Stonisch |
| 7,522,764 B2 | 4/2009 | Schwotzer |
| 7,534,266 B2 | 5/2009 | Kluger |
| 7,536,234 B2 | 5/2009 | Kopelman et al. |
| 7,545,372 B2 | 6/2009 | Kopelman et al. |
| 7,551,760 B2 | 6/2009 | Scharlack et al. |
| 7,555,403 B2 | 6/2009 | Kopelman et al. |
| 7,556,496 B2 | 7/2009 | Cinader, Jr. et al. |
| 7,559,692 B2 | 7/2009 | Beckhaus et al. |
| 7,563,397 B2 | 7/2009 | Schulman et al. |
| D597,769 S | 8/2009 | Richter et al. |
| 7,572,058 B2 | 8/2009 | Pruss et al. |
| 7,572,125 B2 | 8/2009 | Brajnovic |
| 7,574,025 B2 | 8/2009 | Feldman |
| 7,578,673 B2 | 8/2009 | Wen et al. |
| 7,580,502 B2 | 8/2009 | Dalpiaz et al. |
| 7,581,951 B2 | 9/2009 | Lehmann et al. |
| 7,582,855 B2 | 9/2009 | Pfeiffer |
| 7,628,537 B2 | 12/2009 | Schulze-Ganzlin |
| 7,632,097 B2 | 12/2009 | Clerck |
| 7,653,455 B2 | 1/2010 | Cnader, Jr. et al. |
| 7,654,823 B2 | 2/2010 | Dadi |
| 7,655,586 B1 | 2/2010 | Brodkin et al. |
| 7,658,610 B2 | 2/2010 | Knopp |
| 7,661,956 B2 | 2/2010 | Powell et al. |
| 7,665,989 B2 | 2/2010 | Brajnovic et al. |
| 7,679,723 B2 | 3/2010 | Schwotzer |
| 7,687,754 B2 | 3/2010 | Eiff et al. |
| 7,689,308 B2 | 3/2010 | Holzner et al. |
| D614,210 S | 4/2010 | Basler et al. |
| 7,698,014 B2 | 4/2010 | Dunne et al. |
| 7,758,346 B1 | 7/2010 | Letcher |
| 7,774,084 B2 | 8/2010 | Cinader, Jr. |
| 7,780,907 B2 | 8/2010 | Schmidt et al. |
| 7,785,007 B2 | 8/2010 | Stoeckl |
| 7,787,132 B2 | 8/2010 | Körner et al. |
| 7,796,811 B2 | 9/2010 | Orth et al. |
| 7,798,708 B2 | 9/2010 | Erhardt et al. |
| 7,801,632 B2 | 9/2010 | Orth et al. |
| 7,815,371 B2 | 10/2010 | Schulze-Ganzlin |
| 7,824,181 B2 | 11/2010 | Sers |
| D629,908 S | 12/2010 | Jerger et al. |
| 7,855,354 B2 | 12/2010 | Eiff |
| 7,865,261 B2 | 1/2011 | Pfeiffer |
| 7,876,877 B2 | 1/2011 | Stockl |
| 7,901,209 B2 | 3/2011 | Saliger et al. |
| 7,982,731 B2 | 7/2011 | Orth et al. |
| 7,985,119 B2 | 7/2011 | Basler et al. |
| 7,986,415 B2 | 7/2011 | Thiel et al. |
| 7,988,449 B2 | 8/2011 | Amber et al. |
| 8,011,925 B2 | 9/2011 | Powell et al. |
| 8,011,927 B2 | 9/2011 | Merckmans, III et al. |
| 8,026,943 B2 | 9/2011 | Weber et al. |
| 8,038,440 B2 | 10/2011 | Swaelens et al. |
| 8,047,895 B2 | 11/2011 | Basler |
| 8,057,912 B2 | 11/2011 | Basler et al. |
| 8,062,034 B2 | 11/2011 | Hanisch et al. |
| 8,075,313 B2 | 12/2011 | Ranck et al. |
| 8,083,522 B2 | 12/2011 | Karkar et al. |
| 8,105,081 B2 | 1/2012 | Bavar |
| 8,185,224 B2 | 5/2012 | Powell et al. |
| 8,226,654 B2 | 7/2012 | Ranck et al. |
| 8,257,083 B2 | 9/2012 | Berckmans, III et al. |
| 8,272,870 B2 | 9/2012 | Van Lierde et al. |
| 8,602,783 B2 * | 12/2013 | Fudim ............... 433/214 |
| 2001/0008751 A1 | 7/2001 | Chishti et al. |
| 2001/0034010 A1 | 10/2001 | MacDougald et al. |
| 2002/0010568 A1 | 1/2002 | Rubbert et al. |
| 2002/0028418 A1 | 3/2002 | Farag et al. |
| 2002/0039717 A1 | 4/2002 | Amber et al. |
| 2002/0160337 A1 | 10/2002 | Klein et al. |
| 2002/0167100 A1 | 11/2002 | Moszner |
| 2003/0130605 A1 | 7/2003 | Besek |
| 2003/0222366 A1 | 12/2003 | Stangel |
| 2004/0029074 A1 | 2/2004 | Brajnovic |
| 2004/0048227 A1 | 3/2004 | Brajnovic |
| 2004/0121286 A1 * | 6/2004 | Aravena et al. ............... 433/173 |
| 2004/0180308 A1 | 9/2004 | Ebi et al. |
| 2004/0219477 A1 | 11/2004 | Harter |
| 2004/0219479 A1 | 11/2004 | Malin et al. |
| 2004/0219490 A1 | 11/2004 | Gartner et al. |
| 2004/0220691 A1 | 11/2004 | Hofmeister et al. |
| 2004/0241611 A1 | 12/2004 | Amber et al. |
| 2004/0243481 A1 | 12/2004 | Bradbury et al. |
| 2004/0259051 A1 | 12/2004 | Brajnovic |
| 2005/0023710 A1 | 2/2005 | Brodkin et al. |
| 2005/0056350 A1 | 3/2005 | Dolabdjian et al. |
| 2005/0070782 A1 | 3/2005 | Brodkin |
| 2005/0084144 A1 | 4/2005 | Feldman |
| 2005/0100861 A1 | 5/2005 | Choi et al. |
| 2005/0170311 A1 | 8/2005 | Tardieu et al. |
| 2005/0271996 A1 | 12/2005 | Sporbert et al. |
| 2005/0277089 A1 | 12/2005 | Brajnovic |
| 2005/0277090 A1 | 12/2005 | Anderson et al. |
| 2005/0277091 A1 | 12/2005 | Andersson et al. |
| 2005/0282106 A1 | 12/2005 | Sussman et al. |
| 2005/0283065 A1 | 12/2005 | Babayoff |
| 2006/0006561 A1 | 1/2006 | Brajnovic |
| 2006/0008763 A1 | 1/2006 | Brajnovic |
| 2006/0008770 A1 | 1/2006 | Brajnovic et al. |
| 2006/0093988 A1 | 5/2006 | Swaelens et al. |
| 2006/0094951 A1 | 5/2006 | Dean et al. |
| 2006/0127848 A1 | 6/2006 | Sogo et al. |
| 2006/0210949 A1 | 9/2006 | Stoop |
| 2006/0240385 A1 * | 10/2006 | Gatti ............... 433/174 |
| 2006/0252009 A1 | 11/2006 | Gogarnoiu |
| 2006/0263741 A1 | 11/2006 | Imgrund et al. |
| 2006/0281041 A1 | 12/2006 | Rubbert et al. |
| 2007/0015111 A1 | 1/2007 | Kopelman et al. |
| 2007/0031790 A1 | 2/2007 | Raby et al. |
| 2007/0065777 A1 | 3/2007 | Becker |
| 2007/0077532 A1 | 4/2007 | Harter |
| 2007/0092854 A1 | 4/2007 | Powell et al. |
| 2007/0141525 A1 | 6/2007 | Cinader, Jr. |
| 2007/0211081 A1 | 9/2007 | Quadling et al. |
| 2007/0218426 A1 | 9/2007 | Quadling et al. |
| 2007/0269769 A1 | 11/2007 | Marchesi |
| 2007/0281277 A1 | 12/2007 | Brajnovic |
| 2008/0038692 A1 | 2/2008 | Andersson et al. |
| 2008/0044794 A1 | 2/2008 | Brajnovic |
| 2008/0057467 A1 | 3/2008 | Gittelson |
| 2008/0070181 A1 | 3/2008 | Abolfathi et al. |
| 2008/0085489 A1 | 4/2008 | Schmitt |
| 2008/0090210 A1 | 4/2008 | Brajnovic |
| 2008/0114371 A1 | 5/2008 | Kluger |
| 2008/0118895 A1 | 5/2008 | Brajnovic |
| 2008/0124676 A1 | 5/2008 | Marotta |
| 2008/0153060 A1 | 6/2008 | De Moyer |
| 2008/0153061 A1 | 6/2008 | Marcello |
| 2008/0153065 A1 | 6/2008 | Brajnovic et al. |
| 2008/0153069 A1 | 6/2008 | Holzner et al. |
| 2008/0176189 A1 | 7/2008 | Stonisch |
| 2008/0206714 A1 | 8/2008 | Schmitt |
| 2008/0233537 A1 | 9/2008 | Amber et al. |
| 2008/0233539 A1 | 9/2008 | Rossler et al. |
| 2008/0241798 A1 | 10/2008 | Holzner et al. |
| 2008/0261165 A1 | 10/2008 | Steingart et al. |
| 2008/0261176 A1 | 10/2008 | Hurson |
| 2008/0286722 A1 | 11/2008 | Berckmans, III et al. |
| 2008/0300716 A1 | 12/2008 | Kopelman et al. |
| 2009/0017418 A1 | 1/2009 | Gittelson |
| 2009/0026643 A1 | 1/2009 | Wiest et al. |
| 2009/0042167 A1 | 2/2009 | Van Der Zel |
| 2009/0081616 A1 | 3/2009 | Pfeiffer |
| 2009/0087817 A1 | 4/2009 | Jansen et al. |
| 2009/0092948 A1 | 4/2009 | Gantes |
| 2009/0098510 A1 | 4/2009 | Zhang |
| 2009/0098511 A1 | 4/2009 | Zhang |
| 2009/0123045 A1 | 5/2009 | Quadling et al. |

(56) References Cited

U.S. PATENT DOCUMENTS

| | | |
|---|---|---|
| 2009/0123887 A1 | 5/2009 | Brajnovic |
| 2009/0130630 A1 | 5/2009 | Suttin et al. |
| 2009/0186319 A1 | 7/2009 | Sager |
| 2009/0187393 A1 | 7/2009 | Van Lierde et al. |
| 2009/0220134 A1 | 9/2009 | Cahill et al. |
| 2009/0220916 A1 | 9/2009 | Fisker et al. |
| 2009/0220917 A1 | 9/2009 | Jensen |
| 2009/0239195 A1* | 9/2009 | Wohrle et al. .......... 433/174 |
| 2009/0239197 A1 | 9/2009 | Brajnovic |
| 2009/0239200 A1 | 9/2009 | Brajnovic et al. |
| 2009/0253097 A1 | 10/2009 | Brajnovic |
| 2009/0263764 A1 | 10/2009 | Berckmans, III et al. |
| 2009/0287332 A1 | 11/2009 | Adusumilli et al. |
| 2009/0298009 A1 | 12/2009 | Brajnovic |
| 2009/0298017 A1 | 12/2009 | Boerjes et al. |
| 2009/0317763 A1 | 12/2009 | Brajnovic |
| 2009/0325122 A1 | 12/2009 | Brajnovic et al. |
| 2010/0009314 A1 | 1/2010 | Tardieu et al. |
| 2010/0028827 A1 | 2/2010 | Andersson et al. |
| 2010/0038807 A1 | 2/2010 | Brodkin et al. |
| 2010/0075275 A1 | 3/2010 | Brajnovic |
| 2010/0092904 A1 | 4/2010 | Esposti et al. |
| 2010/0105008 A1 | 4/2010 | Powell et al. |
| 2010/0151420 A1 | 6/2010 | Ranck |
| 2010/0151423 A1 | 6/2010 | Ranck et al. |
| 2010/0173260 A1 | 7/2010 | Sogo et al. |
| 2010/0209877 A1 | 8/2010 | Hogan et al. |
| 2010/0280798 A1 | 11/2010 | Pattijn et al. |
| 2010/0330533 A1 | 12/2010 | Cottrell |
| 2011/0008751 A1 | 1/2011 | Pettersson |
| 2011/0060558 A1 | 3/2011 | Pettersson |
| 2011/0123959 A1 | 5/2011 | Sicurelli et al. |
| 2011/0129792 A1 | 6/2011 | Berckmans, III et al. |
| 2011/0159455 A1 | 6/2011 | Stumpel |
| 2011/0183289 A1 | 7/2011 | Powell et al. |
| 2011/0191081 A1 | 8/2011 | Malfliet et al. |
| 2011/0200967 A1 | 8/2011 | Laizure, Jr. |
| 2011/0244426 A1 | 10/2011 | Amber et al. |
| 2011/0269104 A1 | 11/2011 | Berckmans, III et al. |
| 2011/0275032 A1 | 11/2011 | Tardieu et al. |
| 2011/0306008 A1 | 12/2011 | Suttin et al. |
| 2011/0306009 A1 | 12/2011 | Suttin et al. |
| 2011/0306014 A1 | 12/2011 | Conte et al. |
| 2012/0010740 A1 | 1/2012 | Swaelens et al. |
| 2012/0135370 A1 | 5/2012 | Ranck et al. |
| 2012/0164593 A1 | 6/2012 | Bavar |
| 2012/0164893 A1 | 6/2012 | Mitsuzuka et al. |
| 2012/0214130 A1 | 8/2012 | Krivoruk |
| 2012/0330315 A1 | 12/2012 | Ranck et al. |
| 2013/0101964 A1* | 4/2013 | Fudim .......... 433/214 |

FOREIGN PATENT DOCUMENTS

| | | |
|---|---|---|
| WO | WO 99/32045 | 7/1999 |
| WO | WO 00/08415 | 2/2000 |
| WO | WO 01/58379 | 8/2001 |
| WO | WO 02/053055 | 7/2002 |
| WO | WO 03/024352 | 3/2003 |
| WO | WO 2004/030565 | 4/2004 |
| WO | WO 2004/075771 | 9/2004 |
| WO | WO 2004/087000 | 10/2004 |
| WO | WO 2004/098435 | 11/2004 |
| WO | WO 2006/014130 | 2/2006 |
| WO | WO 2006/062459 | 6/2006 |
| WO | WO 2006/082198 | 8/2006 |
| WO | WO 2007/005490 | 1/2007 |
| WO | WO 2007/033157 | 3/2007 |
| WO | WO 2007/104842 | 9/2007 |
| WO | WO 2007/129955 | 11/2007 |
| WO | WO 2008/057955 | 5/2008 |
| WO | WO 2008/083857 | 7/2008 |
| WO | WO 2009/146164 | 12/2009 |

OTHER PUBLICATIONS

Francois Goulette, "A New Method and a Clinical case for Computer Assisted Dental Implantology." Retrieved from Summer European university in surgical Robotics, URL:www.lirmm.fr/manifs/UEE/docs/students/goulette.pdf, Sep. 6, 2003 (7 pages).

Jakob Brief, "Accuracy of image-guided implantology." Retrieved from Google, <URL:sitemaker.umich.edu/sarmentlab/files/robodent_vs_denx_coir_05.pdf, Aug. 20, 2004 (7 pages).

Machine Design: "Robots are ready for medical manufacturing." Retrieved from MachineDesign.Com, <URL: http://machinedesign.com/article/robots-are-ready-for-medical-manufacturing-0712>, Jul. 12, 2007 (7 pages).

MedNEWS: "'Surgical Glue' May Help to Eliminate Suturing for Implants." Retrieved from MediNEWS.Direct, URL:http://www.medinewsdirect.com/?p=377, Dec. 21, 2007 (1 page).

* cited by examiner

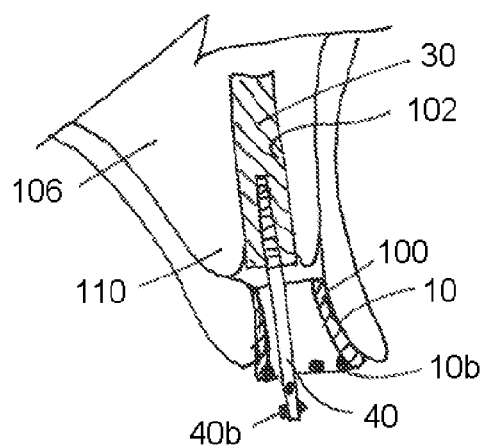
FIG. 9
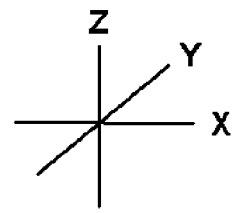
FIG. 10
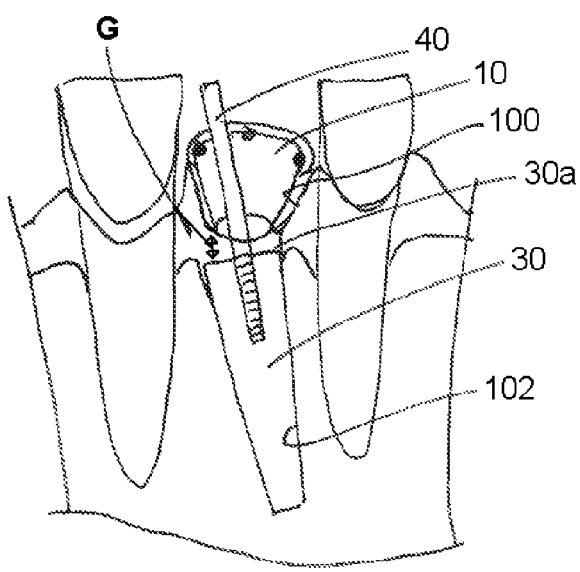
FIG. 11
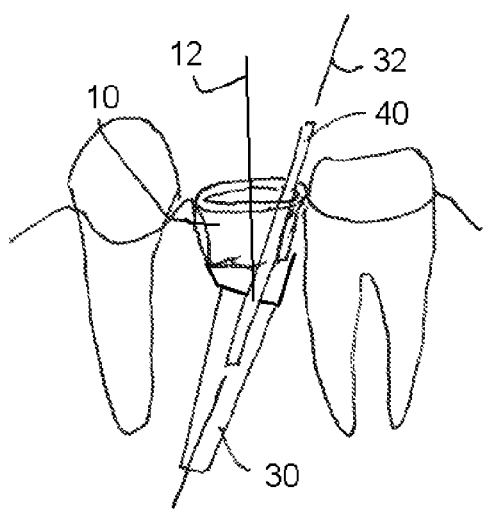

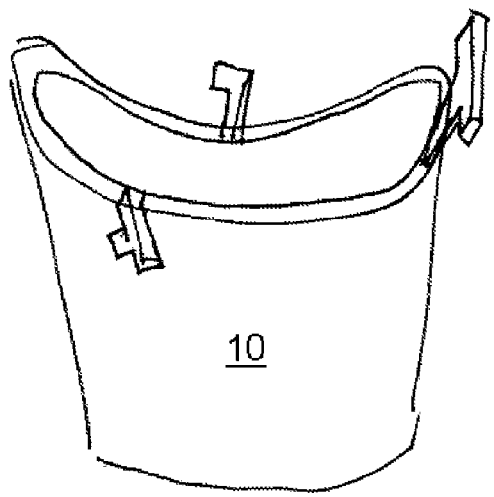
FIG. 16
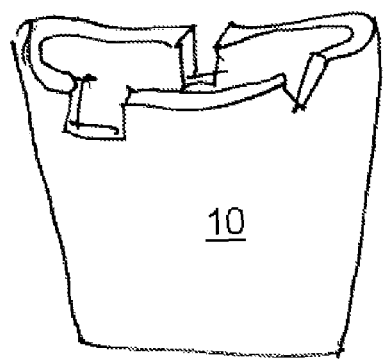
FIG. 17
FIG. 18
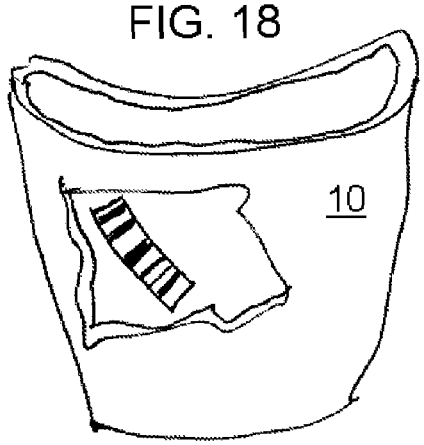
FIG. 19
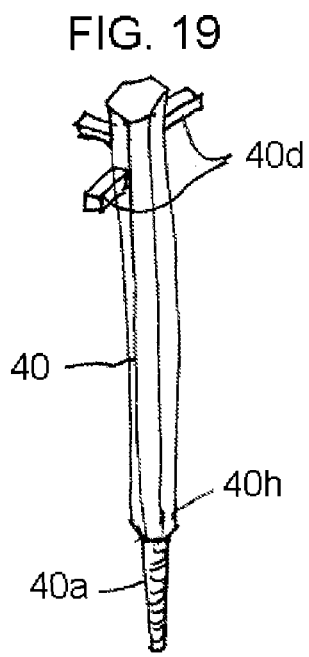

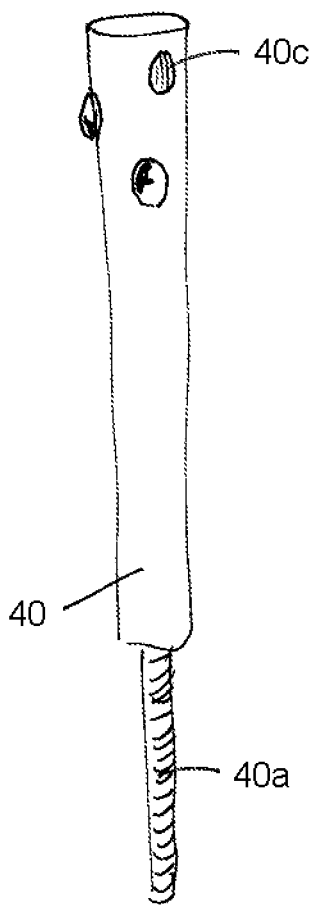
FIG. 20
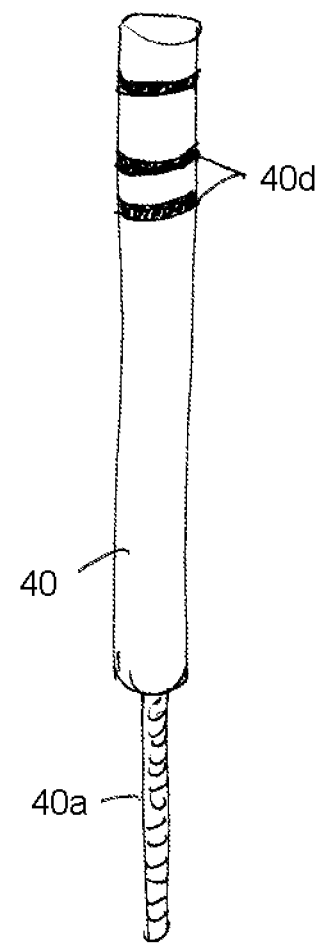
FIG. 21
FIG. 22
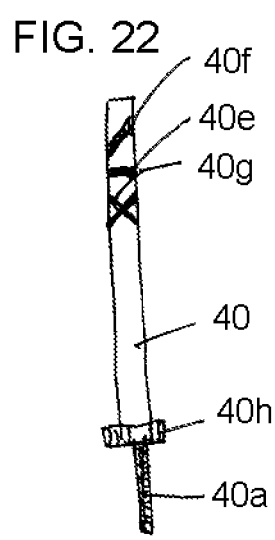
FIG. 23
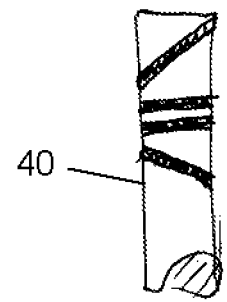

METHOD AND APPARATUS FOR RECORDING SPATIAL GINGIVAL SOFT TISSUE RELATIONSHIP TO IMPLANT PLACEMENT WITHIN ALVEOLAR BONE FOR IMMEDIATE-IMPLANT PLACEMENT

CROSS-REFERENCE TO RELATED APPLICATION

This is a continuation-in-part of application Ser. No. 13/356,359 filed Jan. 23, 2012 which is incorporated herein by reference.

FIELD AND BACKGROUND OF THE INVENTION

The present invention relates generally to the field of dental implants and, in particular, to new and useful soft tissue preservation abutment arrangement and method with immediate implant placement. The invention relates generally to the ability to record the spatial relationship of the residual soft tissue socket of an extraction site, to the position of an immediate implant placed within the alveolar bone without direct contact of the structures. The invention relates generally to recording the individual shape and position of the residual soft tissue socket and how it relates to other structures prior to removal of the tooth, namely the shape and position of the clinical crown of the extracted tooth and the occlusal contact of the opposing and adjacent teeth.

General Considerations and Problems to Overcome:

The tooth is a structure of the oral cavity which is vital to the capability of chewing and important to the general well-being and appearance of people. Anatomically, the tooth resides within the oral cavity, firmly anchored within the upper and lower jaws (maxilla and mandible). Human teeth reside within two distinct anatomic regions of the jaws; the apical inferior portion of the tooth (the root) is connected to the jaw via an attachment called the periodontal ligament. We will here define this portion of the tooth that is connected to the bone as the "bone-zone" or hard tissue zone of the tooth. Second, the superior portion of the tooth (the anatomic crown) is connected to the jaw in the soft tissue or gingival region of the jaw defined as the "tissue-zone" or soft tissue zone. The anatomic crown is demarcated, as that portion of the tooth superior to crest of bone and it will include a small portion of the root superior to the crest of bone as well as the clinical crown that is visible. The tissue-zone forms a soft tissue collar around the neck of a tooth. This tissue-zone connection (i.e. soft tissue to tooth attachment) is composed of gingival fibers that insert into the superior aspect of the root surface; specifically, hemidesmosmal cell attachment to the root and crown forming a biological adhesion of the sulcular epithelium (gingival tissues) to the surface of a tooth.

The tissue-zone connection plays a critical role in maintaining health of the oral cavity. It does this by preventing the ingress of microbes and foreign substances into the body by providing a "biologic-seal" at the interface of the tooth-jaw connection at the tissue-zone. This functional attachment of the soft tissue to the surface of the tooth should be fully appreciated as a critical defense barrier. As without the presence of this soft tissue biologic seal the underlying bone would be vulnerable to numerous invasions of various foreign substances.

In addition, the tissue-zone plays an essential role in maintaining and preserving the dental esthetics of the smile. This same tissue-zone represents the peaks (papillae) and valleys of the soft tissue gingival that surround the neck of each and every tooth. It is the spatial relationship of tooth form and color with healthy soft tissue gingival architecture that are known as the essential building blocks of dental esthetics as we know it. Experts of dental esthetics have called the soft tissue gingiva "the frame" of the picture, and regard the teeth as the "subject matter" of that painting. Disregarding the frame of a painting would certainly impact the overall esthetic appearance being viewed, and the same is true with respect to the gums and teeth. The loss or the alternation of anatomic structures of the tissue-zone has been shown to lead to an inferior esthetic outcome in addition to causing a potential risk of disease for the patient.

The tooth and its attachment to the jaw is subject to numerous pathogens over the lifetime of a patient, particularly due to trauma/fracture, endodontic failure, decay, localized periodontal disease, etc. Any of these conditions can lead to the eventual need for removal of either a single tooth or multiple teeth. The removal or extraction of a tooth or teeth will result in a radical morphologic change to the anatomy as well as the potential exposure of the internal tissues (connective tissues and underlying organs) of the body to invasion by foreign substances.

The extraction of a tooth results in a cascade of changes depending on how this procedure is performed. Tooth removal in the past has been a highly traumatic surgical procedure. It was not uncommon for an oral surgeon to fully reflect the gingival tissues as a surgical flap to expose the underlying tooth and bone to aid in the ease of access and visualization of the tooth to be removed. It is during this surgical reflection of the gingival soft tissues that the normal anatomy of the tissue-zone would be radically altered and permanently changed. Destruction of the normal architecture of the gingiva occurs as surgical instruments were used to cut, tear, crush and rip the attachment fibers between the tooth and soft tissues of the tissue-zone. In accordance with gingival surgical flap surgery, closure of a surgical flap is accomplished with the placement of sutures to close the wound created. Primary (or complete) flap closure is highly desirable to ensure the re-establishment of a biologic-seal of the soft tissue to preventingress of foreign bodies to the host.

Gingival flap surgery also has the known deficiency to result in bone loss from the stripping away of the periosteum and hence the blood supply to the bone during the reflection of a surgical flap. It is well documented in the dental literature that gingival surgical flaps result in bone loss by the exposure of the underlying bone. Dr. Lindhe and co-workers have scientifically demonstrated that surgical flap elevation and removal of teeth leads to loss of the residual bone and the shape of remaining ridge after tooth removal. These undesirable anatomic changes to the bone make the placement of implants more complex and increases risk for patients.

For the reasons identified above, the trend toward minimally invasive surgical procedures has been developed toward the extraction of teeth. Examples of these changes include the use of micro-surgical instruments, periotomes and extraction forceps that do not require the reflection of a surgical flap to remove teeth. Ultrasonic (piezo technology) surgical instruments, dental lasers and rotary devices have been suggested as mechanisms to minimize trauma during the removal of teeth. It is generally accepted within the profession that a minimally invasive technique for tooth removal should be the standard of care.

In an attempt to minimize detrimental anatomic changes during the surgical removal of a tooth, a major effort is now underway to preserve the bone-zone and tissue-zone after tooth removal. The objective of the dental profession to preserve bone was a natural extension of a vast body of knowledge recently created on periodontal bone regeneration via the use of bone replacement substances. Examples of such efforts include autografts, allografts, xenografts and a variety of bone replacement materials that include; Bone Morphogenic Proteins (BMP's), Stem Cell Derivatives, Platelet Rich Proteins (PRP's) derived from the blood and numerous other biologic sources. Bone regeneration after periodontal disease is well established in the prior art. A deficiency of using bone replacement substances is the inability to contain and protect these materials to exposure to the oral cavity during the critical healing phase, i.e. a fundamental inability to re-establish the all-important biologic-seal of the Tissue-Zone once a tooth is removed.

The use of barrier membranes for guided tissue bone regeneration (GTR) is a known attempt to preserve and regenerate lost bone after periodontal disease. The use of membranes has more recently been applied to the regeneration and preservation of bone after tooth removal. Barrier membranes assist in creating a protective barricade to the bone-zone by excluding unwanted cells (connective tissue cells) from the healing site. This is an attempt to allow the body to more effectively refill a residual bony socket with bone cells (a.k.a. osteoblasts) known to be critical for bone growth. A general deficiency of using barrier membranes is the direct exposure of a barrier membrane that consequently lends to the inability to establish a soft tissue seal. The exposure of the barrier membrane leads to plaque accumulation on the surface of the membrane that is impossible to clean. Once membranes become exposed to the oral environment, bacteria colonization on the surface of the membrane quickly spearheads an infection and/or failure of regeneration of bone. The primary cause of the exposure of the membrane is a lack of a soft tissue biologic-seal after gingival flap surgery. The inability to re-establish a biologic-seal after the removal of a tooth has many repercussions to bone and soft tissue regeneration.

A general deficiency of the fresh extraction site is the ability to relate the position of the overlying residual soft tissue to an implant placed immediately into a fresh bony extraction site. The root socket will often dictate where and how the implant will be placed. An angle naturally exists between the clinical crown and the root of a tooth ranging from 5 to 28 degrees in a buccal-lingual direction. Teeth are also known to have a medial or distal tip of the root within the range of 2 to 17 degrees in a properly aligned dentition according to the Kraus, Jordan and Abrams Dental Anatomy and Occlusion textbook. See Kraus B, Jordan R, Abrams L., *Dental Anatomy and Occlusion*, Waverly Press, Inc. Baltimore, Md. 1980. Teeth are often mal-aligned prior to removal and may therefore have root positions with greater angles then those previously mentioned. It is therefore not uncommon that the roots of these teeth would require an immediate implant to be positioned with a significant angulation to the ideal axial position resulting in an angulated post-implant placement. Additionally, the ability to control the vertical, horizontal and transverse positioning of an implant by the operator during immediate implant placement into an extraction site can be difficult as it is often dictated by the remaining bone availability. Bone morphology related to the overlying gingival tissues are considered independent anatomic structures in which the shape and position of one does not dictate the other. This finding is why pre-treatment dental CT-scans are considered the standard of diagnostic care for implant placement. Therefore the location of an immediate implant placed within a fresh extraction site is typically not positioned concentric to the position of the overlying residual soft tissue gingival socket opening. There is typically a discrepancy between the vertical, horizontal and transverse positions of the opening of the soft tissue gingival socket and the axial position of the immediate dental implant so much so that current available implant components are ineffective.

A general deficiency of being able to relate the spatial position of the residual soft tissue gingival socket complicates the ability to fabricate a dental prosthesis from prefabricated "stock" components. The need to utilize customized components to compensate for the disharmony is important to recognize. The independent spatial relationship of the underlying bone (or dental implant) to the overlying gingival tissues becomes difficult or impossible to relate to one another once the tooth is removed. To overcome these discrepancies, the invention will describe a method and device to accurately record the three-dimensional position of the soft tissue gingival socket after a tooth has been removed. It will also describe a method to relate this soft tissue gingival socket to a dental implant placed within the alveolar bone of an immediate extraction/implant surgical placement procedure. Additionally, the invention will describe means to relate the residual soft tissue socket of the gingiva to the position of the extracted clinical crown prior to removal and the occlusal contacts of that crown to the adjacent teeth as well as the opposing teeth, prior to removal. All of the defined relationships are critical to enable the successful fabrication of a dental implant prosthesis.

Loss of the biologic-seal of the tissue-zone also has a significant impact on soft tissue changes to both the macro- and micro-anatomy of the gingiva. It is accepted in the dental literature that the loss of gingival attachment within the tissue-zone leads to the irreversible loss of the interdental papillae and the gingival architecture surrounding a tooth. There are currently no predictable surgical techniques available to correct the gingival changes to vertical height and horizontal dimensional after tooth removal. Much effort has been directed toward preserving the bone after tooth removal but far less effort has been applied to preserving the macro- and micro-anatomy of the tissue-zone after tooth removal.

As will be explained more fully in the following, the method and arrangement of the present invention are effective means to preserve the esthetic and anatomic architecture of the tissue-zone after tooth removal and to relate and record the spatial relationship of this preserved soft tissue socket to the immediate placement of a dental implant. Furthermore, the invention relates the residual soft tissue socket to the position and shape of the extracted tooth as well as the adjacent and opposing teeth.

The understanding of using a minimally invasive technique as well as re-establishing a biologic-seal after tooth removal has been discussed but has not yet been made possible in all cases by known methods and apparatuses. In addition to these important concepts one further concept related to tooth removal is the technique of immediate dental implant placement after the extraction of a tooth/teeth and the ability to relate the anatomic and dental implant structures to one another and to the surrounding teeth.

The replacement of a tooth by a dental implant device is well known in the prior art. It is understood that there are two basic components to the dental implant device; the root-form component held within the bone-zone commonly referred to as the "dental implant" and a second component, the implant anatomic crown composed of an abutment and clinical crown. Both the abutment and clinical crown are typically placed superior to the crest of bone therefore within and superior to the tissue-zone. An implant prosthesis was first described as a surgical method and device that used a fully submerged, non-loaded healing period prior to the connection of the dental implant crown.

The advent of contemporary implant dentistry was first described by Prof. P. I. Branemark in the late 1970's and established the use of a titanium root-form screw to be inserted into the bone placed by using an atraumatic surgical technique described by this researcher/inventor. The method described by Branemark discussed the placement of the dental implant into jawbone of a fully edentulous ridge. He described a method in which the implant would be fully submerged and non-loaded during a healing period of 4-6 months after the dental implant was placed and covered within the bone. Pre-operative conditions therefore required a fully healed ridge in which teeth were previously removed. The method of using a submerged, non-loaded healing period for dental implants remains an approach still widely utilized today.

However, over the past 30 years alternative methods to implant placement have occurred. The following are different methods that have been advocated to the non-submerged, non-loaded implant healing technique.

Advantages and disadvantages will be briefly discussed for each technique.

Delayed, Submerged, Non-loaded Implant Placement Method:

Defined as the method for placing a root-form dental implant into the jawbone. The implant is placed within the bone-zone initially. The pre-operative condition requires an edentulous ridge. The technique describes the placement of the implant into the bone at or below the crest of bone and it is fully covered by primary flap closure. An initial healing for a period of 4 to 6 months is required. A second surgery is required to expose the root-form implant and to connect a healing abutment. Second healing period of 2-3 months is required for soft tissue. Final crown delivery occurs approximately 9 months after the start of treatment.

Deficiencies of this Prior Art Method:
1. Multiple surgeries prior to implant crown placement are required.
2. Requires an edentulous ridge prior to implant placement into the bone-zone resulting in the irreversible changes to the soft tissues of the tissue-zone.
3. Difficult to re-establish a biologic-seal after numerous surgeries and the connection of the implant crown.
4. Increased cost because of multiple surgeries and prosthetic components.
5. Inability to retain the pre-existing soft tissue anatomy prior to tooth removal soft tissue healing results in undesirable changes to the overlying gingival tissues that result in dramatic changes and/or reduction in the height and shape of the interdental papilla. These changes lead to open contacts, open embrasures and affect the final dental implant prosthesis. The resulting open spaces collect food, dental plaque and calculus and put the patient at greater risk to losing additional teeth in the future.
6. An inability to maintain and record the position of the pre-treatment soft tissue gingival anatomy found prior to tooth removal to the underlying alveolar bone and after a tooth has been removed. This positioning of a dental implant is dictated by bone availability with a failure to be able to relate the position of the dental implant to ideal pre-treatment gingival tissues. The delayed approach makes it impossible to position the dental implant relative to vertical, horizontal and transverse, i.e. X, Y, Z axes of the soft tissue opening prior to tooth removal.

Delayed, Non-Submerged, Non-Loaded Implant Placement Method:

Defined as the method for placing a root-form dental implant into the jawbone exemplified by the Straumann, ITI implant company. The implant is placed within the bone-zone initially. The pre-operative condition requires an edentulous ridge. The technique describes the placement of the implant into the bone at or below the crest of bone or within the tissue-zone. A transmucosal healing cap component is used. A healing abutment or "cap" is placed onto the implant that is in direct contact with the soft tissue during the initial bone-healing period of 4 to 6 months. A second surgery is not required to expose the root-form implant. Reformation of the tissue-zone is required. A connection between the implant and the healing abutment is within the tissue-zone.

Deficiencies of this Prior Art Method:
1. Requires an edentulous ridge prior to implant placement into the bone resulting in the irreversible changes to the soft tissues of the Tissue-Zone.
2. Requires flap surgery to place dental implant
3. Difficult to re-establish a biologic-seal after surgery and the connection of the implant crown.
4. Difficult to re-establish soft tissue anatomy to the state it was prior to tooth removal.
5. Healing abutment has a connection interface within the Tissue-Zone, which allows bacteria to adhere impeding wound healing.
6. Increased cost because of multiple components.
7. Loss of the natural anatomic gingival contours after healing of the extraction socket making it difficult if not impossible to identify and record the spatial position of the residual soft tissue gingival to the position of the underlying bone and/or dental implant.

Immediate Root-Form Implant Placement:

A recent trend in implant dentistry that has occurred, that overcomes the deficiency of requiring multiple surgeries, is the immediate placement of a root-form dental implant directly into an extraction socket after tooth removal.

This method deviates from the original protocols established by Branemark and co-workers. The advantage to the simultaneous placement of a root-form dental implant after tooth removal is the reduction of the number of clinical procedures required as well as decreased treatment time. This technique eliminates the need to have the bone ridge healed after tooth removal consequently requiring fewer surgical procedures.

Immediate implant placement requires a mechanical locking of the root-form dental implant into the residual socket-site after a tooth has been removed. Mechanical locking refers to the root-form implant engaging undisturbed bone in an attempt to provide primary mechanical stability of the implant within the extraction socket. Immediate implant placement is highly desirable in comparison to delayed implant placement since it allows the immediate replacement of the tooth at a substantially reduced amount of time when compared to previous method of delayed implant healing.

Immediate implant placement also requires the positioning of a root-form implant to be located into the residual bone socket dictated by the previous position of the root of the tooth. As previously described the root of a tooth has a naturally occurring angle formed between the root axis and of the crown axis of a tooth. There are angles in two orthogonal planes, the anterior-posterior and transverse, the angle ranges from 5 to 28 degrees in a buccal-lingual direction and 2 to 17 degrees in the mesial-distal direction for tooth/teeth in an ideal position. Frequently roots are found to be mal-aligned resulting in significant deviations to the norm. An extracted root anatomy can have an atypical root form that can be curved, bent or positioned in an unusual location within the bone and the adjacent roots of teeth. Therefore, more often then not the root of a tooth is not axially centric to the clinical crown of a given tooth. Additionally the root of a tooth is not positioned centrically between the two adjacent teeth of the extraction site. In fact more often then not the angulation of the root socket and the soft tissue socket are difficult to align. Therefore, the immediate dental implant is typically not centrically located in relation to the opening of the residual soft tissue socket or the adjacent teeth and roots. Compounding this deficiency is the difficulty of vertical positioning of the immediate dental implant as it is related to the residual soft tissue socket. Vertical discrepancies in position make the positioning of current components difficult if not impossible to use at times since they cannot relate the soft tissue anatomy of the residual soft tissue socket effectively since their shapes and orientations were not designed for the immediate soft tissue socket.

Immediate Implant Placement Presents Numerous Risks and Deficiencies with Current Methods Used:

1. An inability to fully engage the entire remaining socket surface after tooth removal, thereby leaving a space (gap) between the surface of the implant and the surface of the remaining bone.

2. An inability to establish a biologic-seal to the overlying soft tissues after a tooth has been removed.

3. An inability to retain bone regenerative materials if a residual gap remains between the surface of the implant and the bone socket.

4. An inability to establish a biologic-seal of the soft tissue over a barrier membrane to protect and contain bone regeneration materials and the blood clot.

5. Inability to preserve the soft tissue architecture of the gingival of the Tissue-Zone.

6. Inability to compensate for the vertical, horizontal and transverse discrepancy between the positions of the immediate dental implant in relation to the overlying soft tissue gingival socket after tooth removal.

7. Inability to relate the position and anatomy of the residual soft tissue socket to the clinical crown of the extracted tooth and the relative position that the soft tissue socket has to the adjacent and opposing teeth.

8. Inability to record the peaks and valleys of the residual soft-tissue gingival socket as current abutment designs that are not designed to mimic the residual soft tissue socket but are circular in design.

The deficiencies of achieving a predictable and esthetic long term outcome when using an immediate implant placement protocol can all be directly attributed to the inability to establish an acceptable biologic adaptation to create an effective biologic-seal in the tissue-zone of the remaining soft tissue socket after removal of a tooth.

The deficiencies of achieving a predictable and long term esthetic outcome of the final implant prosthesis associated with an immediate implant placement protocol can all be directly attributed to the inability to accurately record the spatial relationship of the overlying soft tissue gingival socket to the underlying dental implant. This non-concentric relationship makes it difficult if not impossible to utilize pre-fabricated stock dental implant abutments in all situations when working with immediate implant placement into a fresh tooth extraction site. Current designs of dental implant abutments are two piece components that require a central hole access for the position of the retaining screw which limits the position of these abutments relative to the dental implant. Current dental implant abutment designs which are anatomic are based on the root anatomy and do not take into account the shape of the residual soft tissue socket topography with a peak and valley gingival margin, hence positioning, maintaining and recording the residual soft tissue socket anatomy is difficult if not impossible with the current "anatomic root form designs" of dental implant abutments. Additionally, lack of an ability to record the spatial relationship of the tissue-zone (trans-gingival zone) of the soft tissue socket to the adjacent teeth and opposing arch make it difficult if not impossible to pre-fabricated stock dental implant abutments.

The tissue-zone, i.e. the residual soft tissue gingival socket, represents the critical transition zone between an immediate dental implant and what will be the shape and position of the final implant crown prosthesis. This unique transition zone must compensate for the spatial position of the implant contained in bone and the implant crown in the oral cavity. The tissue-zone (trans-gingival zone) of the gingiva must be considered an independent anatomic structure when compared to the root-form implant and to the position of the clinical crown. Compensation of positioning can only be achieved if the components used to record this structure are independent from both the root-form implant and the clinical crown of the implant prosthesis owning to the natural and avoidable occurring vertical, horizontal and transverse discrepancies.

Immediate implant placement of a root-form dental implant has been shown to effectively osseointegrate by numerous authors (reference included herein). The residual gap that is present between the implant surface and the bone surface requires careful management whether a surgical flap is performed or a non-flapless minimally invasive extraction technique is used. In either of these two approaches, irreversible soft tissue changes have been shown to occur with immediate implant placement after tooth removal. Changes within the tissue-zone are shown to occur as early as 2-3 days after the immediate implant placement.

Other Prior Art:

U.S. Pat. No. 5,417,568 to Giglio discloses a dental prosthesis that is said to accommodate the gingival contours surrounding the implant prosthesis by imitating the gingival contours around natural teeth. Since the abutment is rigidly connected to the implant and must always be axially aligned with the long axis of the implant, the abutment will rarely, if ever, closely engage the entire existing soft tissue socket created when a tooth has been extracted; consequently, inadequate soft tissue socket adaptation exists. Moreover, seldom is the axis of the implant exactly aligned with the axis of the soft tissue socket. Also, although the abutment disclosed by this patent has raised ridges around its outer perimeter, it is symmetrical, and therefore does not mimic the asymmetric anatomy of a soft tissue socket in the gingiva of a patient from whom a tooth has been extracted.

U.S. Pat. No. 5,899,695, Lazzara, et al. discloses an interchangeable healing abutment and impression coping that is described as an anatomic root form but fails to describe a means of preserving and/or relating the position of the overlying residual soft tissue socket to the underlying position of the dental implant. Components were described to have a rigid snap-fit or direct contact with one another allowing a healing abutment and impression coping to be interchangeable components. Lazzara, et al. also discloses a healing abutment shell in U.S. Pat. No. 5,899,697 that is fitted by seating the shell with a positive contact upon the shoulder of the core component of the dental implant thereby limiting the spatial position of the shell to relative position of the dental implant within the alveolar bone. This requirement sets physical limitations in the vertical, horizontal and transverse positions. The components are shown to be concentrically designed and related to one another and require luting and fixating the components together during use. The overall position of the healing abutment is physically dictated by the position of the dental implant and fixation screw within the root-from implant. The reference discloses no structure for maintaining or preserving the contours of the gingival soft tissue socket with the peaks and valleys of the soft tissue socket. There is no description or teaching as it relates to the non-congruous spatial relationship between the underlying root-form implant and residual soft tissue gingival socket. There is no means to record the spatial position of the residual soft tissue socket to the adjacent or opposing teeth of the extracted tooth. Further, and importantly, these teachings only relate to delayed implant placement, not immediate placement.

U.S. Pat. No. 8,185,224 to Powell, et al. discloses a two piece healing abutment that is to be rigidly connected to a dental implant with positional and orientation markings for the purpose to determine the location of the root-form implant. The healing abutment is connected via screw that retains a healing abutment in direct contact to the underlying root from implant. The reference teaches no structure to maintain or preserve or record the contours of the gingival soft tissue socket with the peaks and valleys of the soft tissue socket. The "anatomic abutment" is based on root form that does not mimic the shape of the soft tissue residual socket topography therefore proper positioning and recording is not possible with this design. The root-form implant is shown to be centric and/or rigidly positioned to the healing abutment with markings. There is no description of a means to relate a non-centric position of the healing abutment related to the root form implant. There is no description or means to compensate or record the independent position of the residual soft tissue socket as it relates to the independent position of the root-form dental implant. The healing abutment is dictated by the position of the root-form implant.

Nowhere in the prior art or in current dental implant wisdom is an anatomically shaped and sized abutment in the form of an asymmetric tubular shell used in conjunction with a dental implant, which is not rigidly or concentrically connected to the implant in advance. As a result of the invention here disclosed, the shell can be moved and maneuvered to any orientation with respect to the x-, y- or z-axis in a soft tissue socket to effectively and fully engage the tissue-zone with no space or gap between the outer surface of the shell and the soft tissue socket, independent of the position and axial orientation of the implant in the bony socket. This independent positioning of the abutment shell and the implant is one of several important advancements of this invention over the prior art.

Additionally, the prior art does not describe a hollow shell with peaks and valleys that mimic that which is found in the residual soft tissue gingival socket anatomy. Current designs that claim to be "anatomic abutments" are designed to mimic the root form related to emergence profile and shape of a cross-sectional root form but this does not mimic the shape that is found after an extraction of a tooth as it relates to the residual soft tissue gingival socket. Prior "anatomic abutments" are designed to be used for a delayed implant placement to create an emergence profile based on the root form of a tooth. The present invention is related to retaining, preserving and recording the fresh extraction soft tissue socket to mimics the gingival contour with the peaks and valleys that mimic the soft tissue contour of a soft tissue socket. The prior art does not define the peaks and valleys as described herein that mimics the residual soft tissue gingival socket. A design without the proper peaks and valleys of the transgingival zone as defined herein lacks the ability to accurately record and maintain these tissues.

U.S. Pat. No. RE37,227 to Brodbeck also disclosed a some-what anatomically shaped abutment but again it is axially fixed to an implant so that there is no freedom of movement between the abutment and the implant but rather they are mechanically coupled to each other when being seated in their respective soft tissue and bone sockets so that the position of one is dictated by the position of the other.

An article titled: "*Immediate Placement and Provisionalization of Maxillary Anterior Single Implants: A Surgical and Prosthodontic Rationale*," by Kan at al., *Pract Periodont Aesthet Dent*, 2000; Vol. 12, No. 9, pps 817-824, discloses the building up of an abutment that is fixed to an implant to better match a soft tissue socket by the addition of autopolymerizing acrylic resin around the abutment by sculpting the outer shape of the otherwise fixed abutment to better fill the soft tissue socket. This technique also fails to recognize the advantage of independently positioning the abutment from the implant. In addition, the tissue-zone collapses immediately upon tooth removal and extrapolation of its contours by the author is required to recreate as close as possible the soft tissue-zone profile.

Another attempt at accommodating the mismatch between an implant oriented in a bony socket and an abutment positioned in a soft tissue socket, is suggested in the June 2009 brochure of BIOMET 3i titled "*Ideal Solutions For Immediate Aesthetics*" that discloses an abutment-implant combination where the abutment axis is at a fixed but non-aligned angle to the implant axis. Here again there is independent positioning of the abutment and the implant so freedom of orientation is not present.

SUMMARY OF THE INVENTION

It is an object of the present invention to solve the problems of the prior art identified above, by providing means for recording the anatomy and the spatial relations of the independent components of the oral cavity after a tooth is removed and an immediate implant is placed into a fresh extraction site. The independent components are defined as follows:

1) The shape and spatial position of the clinical crown of the extracted tooth relative to the other dental components discussed.

2) The shape and spatial position of the inter-occlusal contact to the clinical crown of the extracted tooth prior to removal of the tooth which is relative to the other dental components discussed.

3) The shape and spatial position of an immediate dental implant placed within the bone, and its relative position to the other dental components discussed.

4) The shape and position of the residual soft tissue socket anatomy of the gingiva at an extraction site relative to the position of the other dental components discussed.

Additionally, this is achieved with non-connected components that are independent from one another.

A hollow shell with orientation and dimensional markings is used to record and to preserve the soft tissue anatomy. The hollow shell provides soft tissue preservation as well.

The hollow shell has an interior volume and a shell axis, an outer bio-compatible surface for engaging a soft tissue socket that is left in gingival tissue after a tooth has been extracted from a bone socket under the gingival tissue, a first perimeter adapted for placement toward the bone socket and a second perimeter adapted for placement adjacent an outer surface of the gingival tissue around the soft tissue socket. The first perimeter is smaller than the second perimeter so that the shell tapers outwardly from the first to the second perimeters, the second perimeter being asymmetrically scalloped with opposite distal and mesial peaks and opposite lingual and facial valleys between the peaks. The shell is sized for closely engaging against the soft tissue socket without gaps.

This is only made possible if, in all cases, there is complete freedom of orientation between the shell and the implant-plus-post that allows independent positioning between these two components. In one embodiment of the invention markings are provided on the shell and post and the shell and post in their independent positions and with position markings are scanned and imaged and this image data is used to fabricate abutments, temporary and even permanent crowns. In another embodiment of the invention, luting is used to fill in between the shell and post and rather than, or in addition to the position data being recording, the luting fixes or freezes the shell at its own orientation as dictated by the soft tissue socket, to the post at its own orientation as dictated by the boney socket.

The invention also includes a dental implant having an implant axis and being adapted for placement in the bone socket, a temporary post rigidly connected to and coaxial with the dental implant, the temporary post extending in the interior volume of the hollow shell, and either markings on the post and/or a luting compound filling the interior volume between the shell and the temporary post and setting solid for fixing the shell to the dental implant with no other connection between the shell and the implant so that the outer surface of the shell engages against the soft tissue socket without gaps and without requiring alignment of the shell axis to the implant axes.

The dental implant connection post has orientation and dimensional markings that provide spatial positioning of the dental implant within the bone. The connection post may also serve for retention of materials.

A further and more general object of the invention is to provide a dental implant method and arrangement that uses a hollow shell with physical or visual orientation markings to record the spatial relationship of the residual soft tissue gingival socket to the spatial relationship of the underlying dental implant. The shell is imbued with distinct identification and orientation indications. The markings may be of a design of physical markings, such as indents, detents, internal or external tabs or wings and/or visual markings, laser etching, decals, colored markings or other means of recording spatial orientation of the hollow shell and it's relationship to the residual soft tissue gingival socket. The markings will also code for the physical shape and dimensions of the hollow shell selected for use. The peaks and valleys of the design mimic the shape and contour of the residual soft tissue socket allowing the hollow shell to be positioned relative to the natural occurring peaks and valleys of the residual soft tissue socket opening. A variety of hollow shells are available with different lengths, widths, shapes and diameters in three dimensions of space. The implant spatial relation of the dental implant is recorded from physical markings, detents, indents or visual markings on the temporary post rigidly connected to and coaxial with the dental implant. Recording can be achieved via a variety of means including but not limited to physical dental impressions, CAD/CAM, Digital Impressions, X-Ray computer tomography or other means (digital or physical) to make record of dental casts.

A further object of the invention is to record the three dimensional anatomy of the soft tissue gingival extraction socket so that it's specific soft tissue contour can be replicated without distortion or dimensional changes that occur after tooth removal.

The spatial relationship of soft tissue gingival socket is recorded relative to the temporary connection post that is rigidly connected to and coaxial with the dental implant, the temporary post extends through and above (coronal) in the hollow shell. The connection post is imbued with distinct identification and orientation indications upon the connection post. The markings may be of a design of physical markings, such as indents, detents, internal or external tabs or wings and/or visual markings, laser etching, decals, colored markings or other means of recording spatial orientation of the connection post and its relationship to the residual soft tissue gingival socket. The markings will also code for the physical shape and dimensions of the connection post selected for use. A variety of connection posts are available with different lengths, widths, shapes and diameters in three dimensions of space.

The residual soft tissue socket spatial relation relative to the immediate dental implant can be recorded by a variety of means, not limited to, physical dental impressions, CAD/CAM, Digital Impressions, X-Ray computer tomography or other means (digital or physical) to make record of dental casts. This relationship between the residual soft tissue gingival socket relative to the underlying spatial position of the dental implant and is recorded using a spatial referencing system in the X, Y and Z, i.e. horizontal, vertical and transverse planes. Upon recording the spatial relation of the dental implant to the residual soft tissue gingival socket a variety of temporary and permanent prosthetic components can be fabricated. Importantly the implant prosthesis components could also be recorded and referenced to the remaining dentition by electronic or physical dental impressions to fabricate a dental prosthesis that is spatially related to the adjacent teeth and gingival tissues. It is also possible to take a pre-operative digital scan or pre-operative impression so that the replication of the clinical crown of the removed tooth can be electronically or physically available for fabrication of the prosthesis and its components. Fabrication via laboratory techniques that include direct, indirect dental laboratory fabrication, digital, CAD/CAM, digital milling, etc. can be used. The prosthetic components include a customized abutment that can replicate and compensate for the non-concentric positioning of the implant relative to the residual soft tissue gingival socket. The prosthetic transmucosal component of the final dental implant prosthesis can be fabricated of a variety of materials including but not limited to acrylic or zirconia.

A further object of the invention is to provide a dental implant method and arrangement that uses a hollow shell with outer bio-compatible surface (e.g. of plastic) for engaging a soft tissue socket that is left in gingival tissue immediately after a tooth has been extracted to promote healing by independently positioning the shell and the implant that has been fixed in the remaining bony socket, the shell being tapered outwardly from a first to a second perimeter, the second perimeter being asymmetrically scalloped with opposite distal and mesial peaks and opposite lingual and facial valleys between the peaks, the dental implant in the bone or bony socket left after tooth extraction being rigidly connected to a temporary post, the temporary post extending in the shell, and either markings provided on the shell and post for recording image data for abutment or crown fabrication, or a luting compound filling the volume between the shell and the post and setting solid for fixing the shell in its position and orientation as dictated by the soft tissue socket, to the post and dental implant in their position and orientation as dictated by the boney socket, with no other connection between the shell and the implant so that the outer surface of the shell engages against the soft tissue socket without gaps and without requiring alignment of the shell and implant axes.

Other objects of the invention are to use the shell as a biological seal for both the soft tissue socket and for the bony socket, to preclude contaminants from the soft tissue and from the bony sockets.

Another object of the invention is to use the shell as a foundation for a temporary prosthetic tooth for immediately cosmetically replacing an extracted tooth.

Other objects of the invention will become apparent after considering the following more detailed disclosure of the invention.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 9 is a composite sectional view of the invention with a hollow shell and a connection post;

FIG. 10 is a composite sectional view of the invention with the hollow shell with three distinct visual markings on the occusal edge of the coronal surface and a connection post also with distinct visual markets;

FIG. 11 is a view similar to FIG. 10 showing the dental implant at a different angle to illustrate the real-world variations in position and angle the exist in actual tooth roots;

FIGS. 12 to 18 are side views of embodiments of shells of the invention with different types of markings;

FIGS. 19 to 26 are side views of connecting posts of the invention with different types of markings;

DESCRIPTION OF THE PREFERRED EMBODIMENTS

Figure 1:
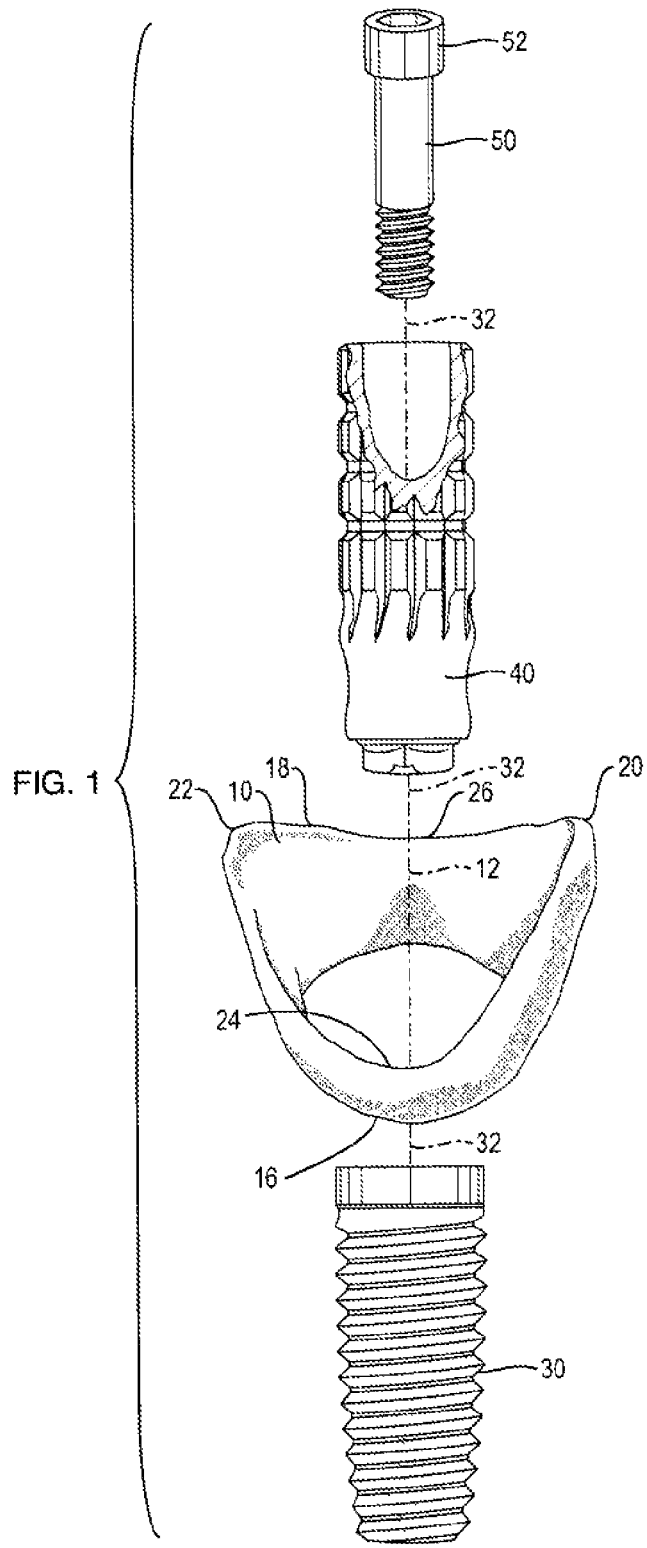
FIG. 1 is an exploded view of important part of the arrangement of the invention.

Apparatus and Arrangement of the Invention:

Referring now to the drawings, in which like reference numerals are used to refer to the same or similar elements, FIG. 1 illustrates a soft tissue preservation, dental implant arrangement that comprises a hollow shell 10 with an interior volume and a shell axis 12. The shell is advantageously made of zirconium dioxide ($ZrO_2$) ceramic material that is known to be bio-compatible. The hollow shell 10 thus has an outer bio-compatible surface for engaging a soft tissue socket that is left in gingival tissue after a tooth has been extracted from a bone or bony socket under the gingival tissue. Shell 10 has a first lower perimeter 16 adapted for placement toward the bone socket of a lower mandibular, tooth. The first or inner perimeter 16 may be an upper perimeter if the shell is to be used for replacing of an extracted upper or maxillary tooth so that terms like "upper" and "lower" as used here are only relative terms and do not convey an absolute position or limitation of the invention.

Shell 10 also has a second or outer perimeter 18 adapted for placement adjacent an outer surface of the gingival tissue, around the soft tissue socket. The first perimeter 16 is smaller than the second perimeter 18 so that the shell 10 tapers outwardly from the first to the second perimeters to anatomically mimic the shape of the soft tissue socket that remains immediately after a tooth has been extracted, and before the soft tissue socket starts to shrink or shift from the natural size, shape and position it had around the patient's natural tooth before extraction.

To further anatomically mimic the shape of the soft tissue socket, the second perimeter 18 is also asymmetrically scalloped with opposite distal and mesial peaks 20 and 22, and opposite lingual and facial valleys 24 and 26, between the peaks. The shapes, sizes, locations and heights of the peaks and valleys are selected to mimic known tooth types, e.g. maxillary or mandibular, central or lateral incisors, canines, premolars and molars, and the shell is also sized for closely engaging against the soft tissue socket without gaps of many tooth shapes, types and sizes. This sizing and shaping is achieved by providing the practitioner with a set or selection of different shell shapes, sizes and types, so that a shell 10 that is close in fit to the soft tissue socket is available, so that the shell engages the soft tissue socket without gaps and thus forms a biological or biologic-seal to preclude contaminants from the soft tissue socket and from the bony socket in the bone under the soft tissue.

As will be explained more fully in the following, the present invention allows this placement of the properly sized and shaped shell 10, in the soft tissue socket, with complete freedom of motion in the x-, y- and z-directions and, just as importantly, with complete freedom of rotation about all three axes. This is done by independently positioning the abutment that is formed by this shell from the solid implant and its connected post that must be rigidly fixed in the bony socket at its own optimum angle and depth.

A dental implant 30 having an implant axis 32 is provided and is adapted for placement in the bone socket immediate after tooth extraction, clearing and dressing of the bony socket in a conventional manner, for example, by removing debris and drilling an immediate implant receiving bore in the bone or bony socket using known techniques.

A temporary post 40 is then rigidly connected to and is coaxial with the dental implant 30, for example, by using a screw 50 that is inserted into a central bore in the post 40 and screwed into a treaded bore in the top center of the implant 30. A head 52 engages an annular step in the post 40 in a known manner, to fix the post 40 to the implant 30. The temporary post 40 extends in the interior volume of the hollow shell 10 but is not yet connected to the shell, and need not even touch the shell, so that despite the fixing of the post to the implant, the shell can be engages to the soft tissue socket without directional or rotational limitation.

Figure 6:
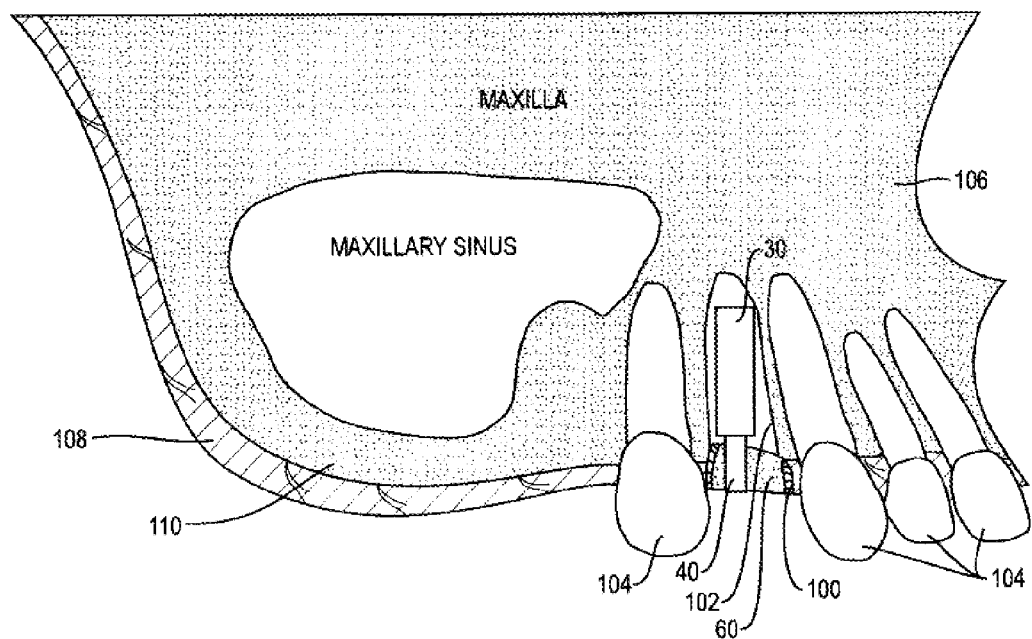
FIG. 6 is a sectional view of the arrangement of the invention after a luting compound has been applied.
Figure 8:
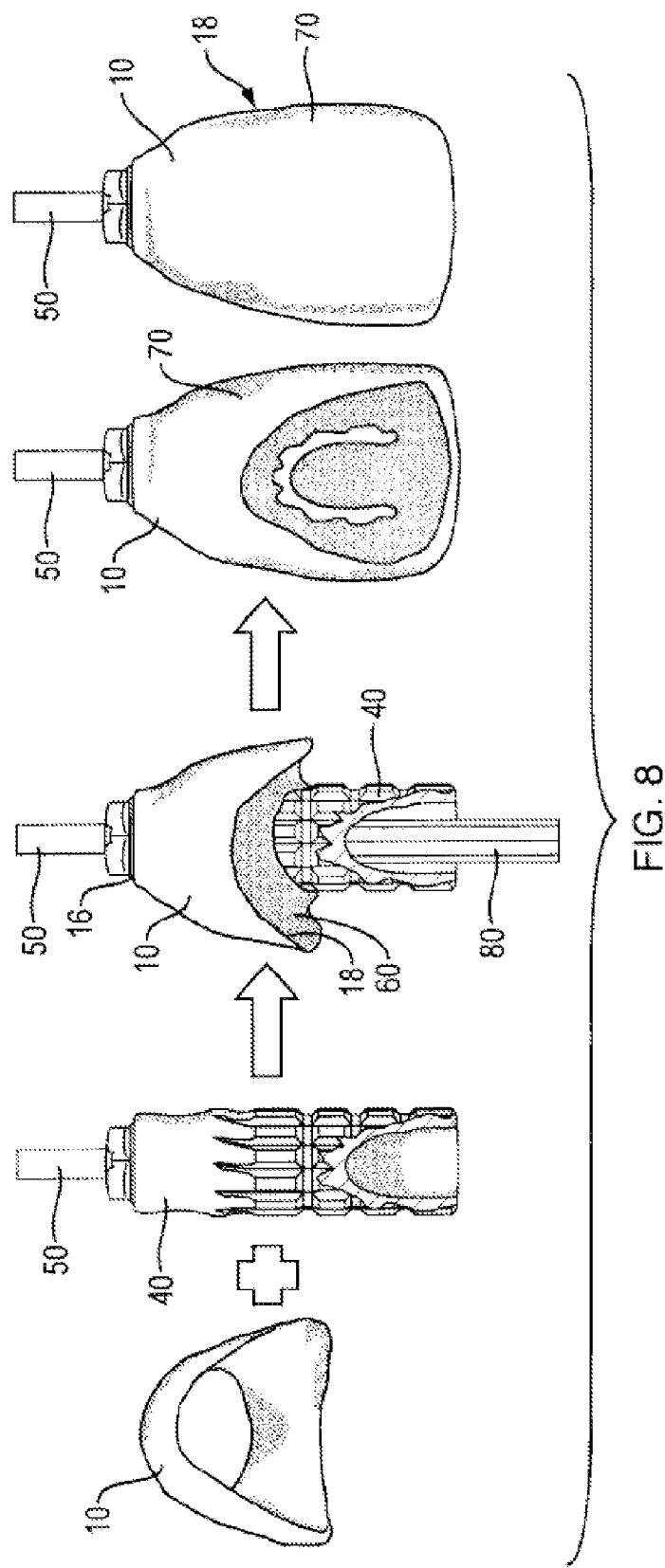
FIG. 8 is a composite view of parts of the arrangement of the invention in a sequence showing an assembly of the parts of the arrangement.

An initially fluid luting compound shown at 60 in FIGS. 6 and 8, is filled into the interior volume between the shell 10 and the temporary post 40 and is allowed to set solid. Only then is the shell 10 fixed to the dental post 40 and implant 30, with no other previous connection between the shell and the implant so that the outer surface of the shell engages against the soft tissue socket 100 without gaps and without requiring any alignment between the shell axis 12 and the implant axes 32. This also seals the bony socket 102 in the jaw bone 106, which, in the case of FIG. 6, is the maxilla that is shown to have other teeth 104 on opposite sides of the extracted tooth socket 102. The inner surface of shell 10 is adapted to adhere well to the luting compound 60 for this embodiment of the invention. This is done by making the shell, and therefore its inner surface, of a material that adheres well to the luting compound, e.g. zirconia, or by treating the inner surface, e.g. by roughening its texture, or by applying a special coating to the inner surface that adheres well to the shell material and to the luting compound when the compound hardens.

Figure 2:
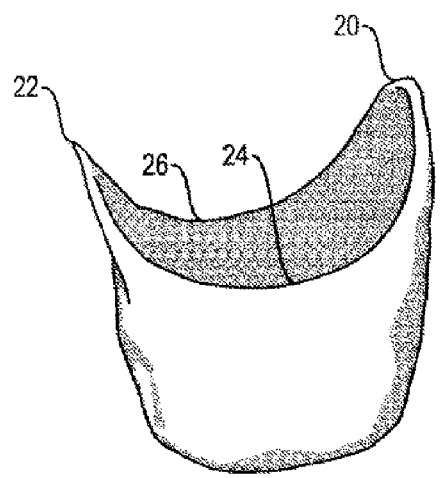
FIG. 2 is a perspective view of a different embodiment of the shell of the invention for use in replacing a different tooth type.
Figure 3:
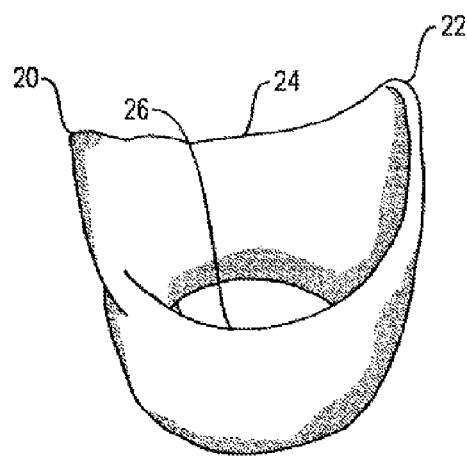
FIG. 3 is a perspective view of a still further embodiment of the shell of the invention for use in replacing a different tooth type.
Figure 4:
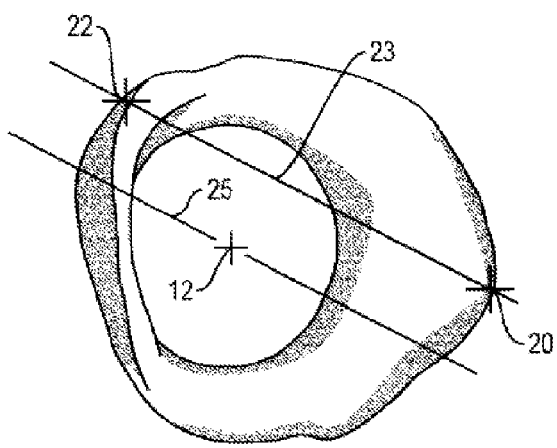
FIG. 4 is a perspective view of an embodiment of the shell of the invention that illustrated the asymmetry of the outer perimeter of the shell.
Figure 5:
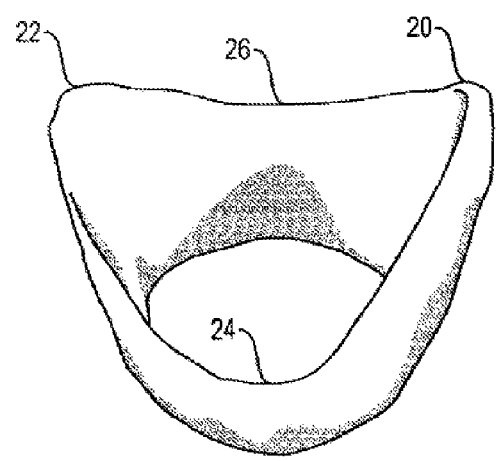
FIG. 5 is a perspective view of the shell of the invention shown also in FIG. 1 for comparison with the shell shapes of FIGS. 2 to 4.

As illustrated in FIGS. 1 and 5, the lingual valley 24 is lower than the facial valley 26 for mimicking maxillary and mandibular incisors for example. For mimicking maxillary and mandibular canines, the valleys 24 and 26 can be of substantially equal in height as illustrated in FIG. 2. For premolars and molars, the opposite of incisors is true so that as shown in FIG. 3 the lingual valley 26 is higher than the facial valley 24 and mesial and distal peeks 20 and 22 are not as highly scalloped as in incisors. Also for some or perhaps most tooth types, the distal and mesial peaks 20 and 22, as shown in FIG. 4, are not in a common plane 23 with the plane 25 extending through the shell axis 12. The asymmetry is also selected to more closely mimic the true shape and size of a soft tissue socket before it starts to deteriorate. These rules are not absolute since there can always be exceptions and variations to the rules because dental anatomy varies and may sometimes reside outside the norms. The set of shell in various sizes, types and shapes provided to the practitioner can accommodate to these variations by allowing the practitioner to select a shell for a different tooth replacement type or, in extreme cases, may arrange for a custom made shell for a particular patient.

Other parts that may be included as part of the arrangement of the invention to be explained later in this disclosure, include a tooth form temporary 70 in FIG. 7, that can be fixed to the outer perimeter 18 of the shell 10, after it has been luted to the post 40, so that the patient has a temporary tooth replacement before leaving the dental office. The arrangement may also includes a cylindrical nylon plug 80 in FIG. 8, that is used to temporary plug the interior volume of the post 40 above the securing screw 50, before the luting step, so that access to the head 52 of the screw 50 can be reestablished when a permanent tooth replacement is to be attached to the implant, or at other points in the process of the invention, by extracting the plug.

Methods and Procedures of the Invention:

With reference to FIGS. 6 and 8, the method of the invention permits immediate implant soft tissue abutment temporary placement at the time of tooth extraction to re-establish an effective biologic-seal of the soft tissues to the surface of the abutment or shell more effectively to its anatomic shape.

The immediate implant soft tissue abutment temporary may be:

1. An immediate soft tissue implant abutment temporary extending from the crest of bone 110 to the height of the remaining soft tissues 108. The immediate soft tissue abutment temporary will re-establish a biologic-seal preserving the gingival soft tissues after the removal of a tooth and the immediate placement of an implant. It also enables containment of bone regenerative materials and primary coverage of the barrier membrane if used after tooth removal; and/or 2. An immediate tooth-form implant temporarily re-establishes a biologic-seal preserving the gingival soft tissues after the removal of a tooth and the immediate placement of an implant. It also enables containment of bone regenerative materials and primary coverage of the barrier membrane if used after tooth removal.

The immediate implant soft tissue abutment temporary is a temporary component that connects to the implant-platform (superior surface of the implant platform) at the bone crest 110 and extends to the level of the free-gingival margin of the soft tissue 108. It provides the necessary shape and adaptation to re-establish a biologic-seal between the soft tissues and the surface of the temporary.

Figure 7:
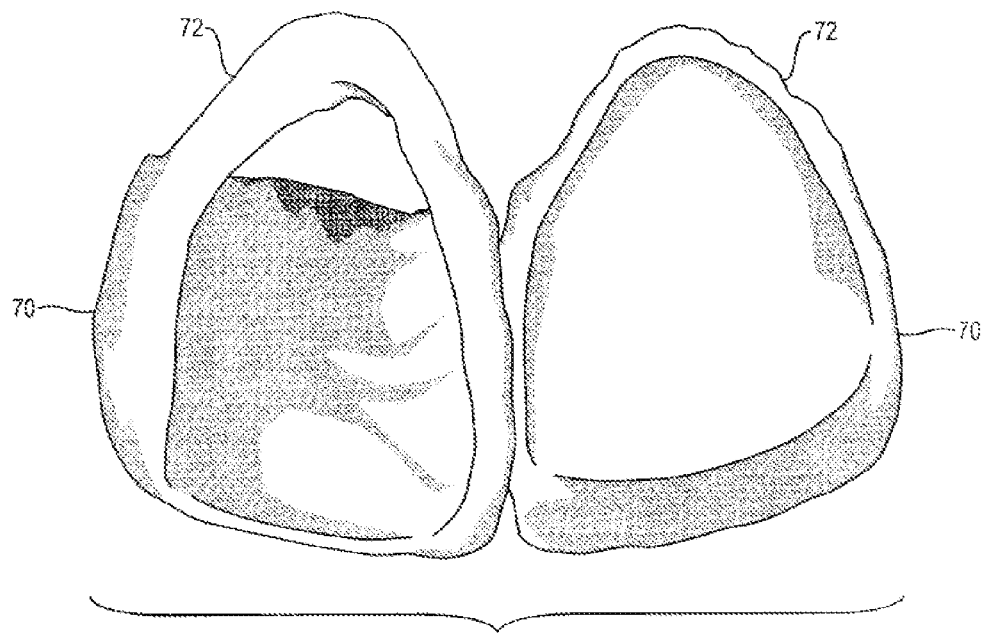
FIG. 7 is a composite, side-by-side, rear (lingual) and front (facial) perspective view of an immediate tooth-form temporary of the invention.

An immediate tooth-form temporary (provisional) 70 of the invention is shown in FIG. 7 and is a temporary component who's subgingival transmucosal section 72 is shaped similar to a root surface and represents the immediate transmucosal temporary (Provisional) described above and who's supragingival component is shaped like a tooth. It is composed of a shell 70 that extends from the implant-platform of the invention that includes the luted shell 10, and extends from the outer perimeter 18 of shell 10 beyond the level of the free-gingival margin to the incisal edge or occlusal surface of the dental tooth it is replacing. Tooth form 70 comes in a variety of different vertical heights, elliptical shapes and different dimensions to temporally replace the various types of teeth that might be extracted. It will be provided to dentist as a kit in which a variety of different sizes, shapes and types are available to replace different teeth that are extracted.

Critical to the design is creating an effective biological socket-seal between the surface of the abutment-temporary (provisional) to adequately support and seal the residual soft tissue socket at the time of placement. The subgingival shape of the abutment-temporary (provisional) promotes biological socket seal by providing either an over-contoured or under-contoured emergence profile to compensate for the position of the dental implant.

Additionally, the abutment-temporary design provides a single uniform material within the soft tissue zone of the residual soft tissue socket that prevents a micro- and macroscopic gap between dissimilar materials in the soft tissue gingival zone.

The abutment-temporary subgingival emergence profile provides an over-contoured or under-contoured shape that is anatomical to compensate for the three dimensional position of the underlying endosseous implant spatial position.

The abutment-temporary dental implant prosthesis is designed to be an interim prosthesis that is fabricated chairside and is customized to provide individual unique tooth replacements. The temporary shell is designed from a series of elliptical and asymmetric shapes that have an eccentric opening for access to accept a cylindrical component that is attached via a screw mounting to the dental implant.

A self-curing material is used to affix the shell to a screw-retained temporary post 40 during the chairside fabrication of the abutment-temporary. The abutment-temporary (provisional) is modified chairside to generate a unique final shape and provide an adequate seal between the abutment-temporary (provisional) and the soft tissue socket. Preformed non-concentric elliptical shells provide a matrix to fabricate the abutment-temporary dental implant restoration.

The immediate abutment-temporary, that can also be thought of as an immediate provisional abutment, has one interface region between the dental implant and the overlying abutment-temporary. The interface is at the level of the implant buccal plate and contained at the level of bone crest. This eliminates the micro- and macroscopic gap from being positioned within the soft tissue zone of the soft tissue residual socket for immediate implant placement into a fresh extraction site.

Additional Embodiments:

With reference now to FIG. 9, hollow shell 10 may have markings, e.g. three distinct visual markings 10b (i.e. holes) on or near the occusal edge or outer, second perimeter 18 of the coronal surface of the peaks and valleys of the shell are seen in a side sectional view through the bone 110 and gingiva 108 of a patient. A connection post 40 with other distinct visual markets 40b is also provided and has been screwed into the dental implant 30. Markings 10b and 40b for both component 10 and 40 provide alignment information so that the physical dimensions of the components are recorded as well. The hollow shell 10 must not make physical contact with the connection post 40 and/or the dental implant 30. Scanning of the image of the marked shell 10 and post 40 using any number of known scanning techniques as will be explained later, records the exact position and relationships of the shell and post with respect to the implant 30. This information can be used to create a correctly sized and oriented healing abutment or temporary crown or even a permanent crown that will properly connect to the implant and that will closely engage the soft tissue socket.

FIG. 10 shows a front view of the area of FIG. 9 to better illustrate the markings and orientation of the shell 10, post 40 and implant 30, showing the three distinct visual markings on the occusal edge of the coronal surface. The connection post 40 with similar distinct visual markets is again noted. Markings for both components are embedded with information so that the physical dimensions of the components are recorded as well. It is noted that a gap G is present between the implant shoulder 30a and the shell 10. Axial orientation of the two components is dissimilar so that each is oriented as needed, i.e. the implant 30 the tooth root and the shell 10 to the soft tissue socket. Recording the relative position of the hollow shell and its relationship to the connection post 40 can be established by scanning. This relationship between the residual soft tissue gingival socket 102 relative to the underlying spatial position of the dental implant is recorded using this spatial referencing system in the X, Y and Z, i.e. horizontal, vertical and transverse planes.

The shell is hollow with distinct markings and is of generally tubular design to accommodate to the position of an immediate root-form implant 30 positioned at multiple locations within the residual socket 102. The hollow shell does not make contact with the immediate root-form implant or the connection post that is rigidly fixed to the root-form implant.

The method and apparatus in the preferred embodiment provide a connection post rigidly fixed to the implant that has distinct markings. The connection post 40 is connected to the root-form implant 30 by screw, frictional interference or other means of securing the connection post to the root-from implant. The connection has distinct identification and orientation indications as noted. The markings may be of a design of physical markings, such as indents, detents, internal or external tabs or wings and/or visual markings, laser etching, decals, colored markings or other means of recording spatial orientation of the connection post and its relationship to the root-form implant. The markings will also code for the physical shape and dimensions of the connection post selected for use. A variety of connection posts are made available with different lengths, widths, shapes and diameters in three dimensions of space.

The method and device provides means to physically or digitally record the spatial relationship of the two non-concentric components. It is possible that the components do not make physical contact with one another. The orientation markings on both the hollow shell and connection post enable the relative position of the two components to be recorded in spite of small or large discrepancies in the x, y, z dimensions. Once the spatial relationship is digitally or physically recorded Analogue components (physical or digital) can be used to fabricate a physical or electronic model. Fabrication of a variety of prosthetic components can be initiated. The prosthetic components can be a temporary abutment, temporary abutment with crown, two piece crown and abutment and/or monolithic temporary restoration or final restoration. Importantly the prosthesis components would be also be recorded and referenced to the remaining dentition by electronic or physical dental impressions so that the fabrication of the prosthesis and it components are spatially related to the remaining teeth and gingival tissues. It is also possible to take a pre-scan or pre-op impression so that the replication of the clinical crown of the tooth removed can be electronically or physically available for the fabrication of the prosthesis and its components.

The method and device promotes cellular soft tissue adherence to the surface of the immediate implant soft tissue temporary (Provisional) abutment.

The method and device preserves the soft tissue architecture of the gingival surrounding the immediate implant soft tissue temporary (Provisional) abutment.

The method and device enables bone regenerative materials to be retained in any gap left around the top of the implant 30, and protected during initial healing but the shell, in effect, sealing this area from the outer end of the soft and bony sockets.

The immediate implant soft tissue abutment temporary, i.e. shell 10, method has the following features or steps.

The method and device in the preferred embodiment uses a surgically sterile surface for shell 10 with distinct identification and orientation indications upon the hollow shell. The markings may be of a design of physical markings, such as indents, detents, internal or external tabs or wings and/or visual markings, laser etching, decals, colored markings or other means of recording spatial orientation of the hollow shell and its relationship to the residual soft tissue gingival socket. The markings will also code for the physical shape and dimensions of the hollow shell selected for use. A variety of hollow shells are made available with different lengths, widths, shapes and diameters in three dimensions of space. The hollow shell creates an intimate to fit to the socket anatomic shape at the time of tooth extraction. A variety of pre-fabricated hollow shells are provided with different sizes and shapes that confirm to the residual soft tissue gingival socket. The hollow shell surface is of a bi-layer micro-texture to promote immediate soft tissue repair and adaptation promoting re-attachment or repair to the biologic surface. It is anticipated that the surface may have a regular micro-geometric pattern that is uniform. It is also anticipated that the surface texture may be modified chairside using a rotary instrument such as a uniquely designed dental bur, that results in a ordered microgeometric repetitive surface pattern in the form of alternating ridges and grooves, each having a unfixed width in a alternating range of about 2.0 to about 25 microns (micrometers) and a nonfixed or altering depth in a range of about 10 microns to about 50 microns, in which the microgemoetric repetitive patterns define a guide soft tissue preservation and re-attachment the soft tissue fibers to the surface of the immediate implant soft tissue temporary abutment.

Figure 12:
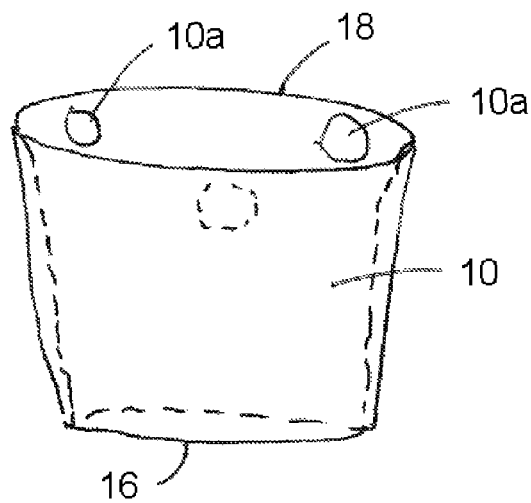
Figure 13:
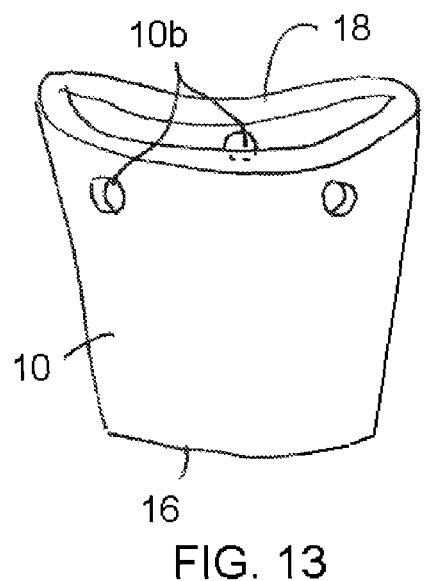
Figure 14:
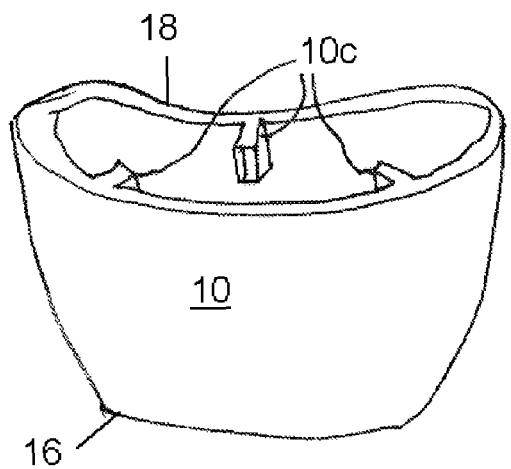
Figure 15:
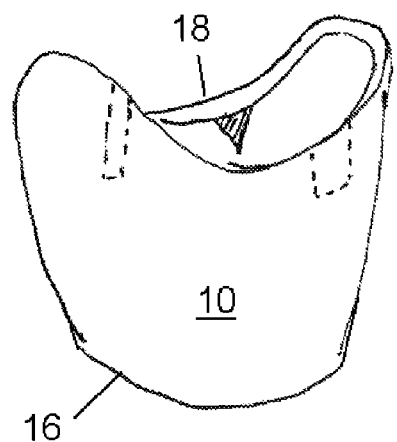
Figure 24:
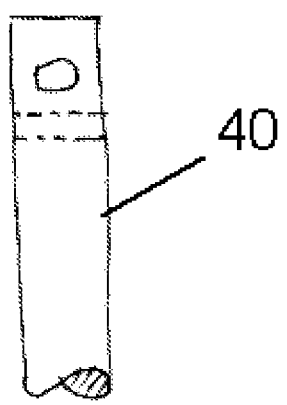
Figure 25:
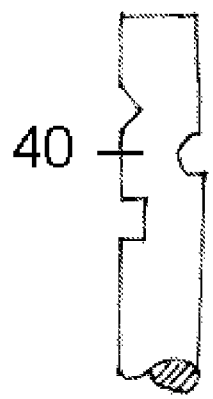

In FIG. 12, the shell 10 has markings in the forms of three inwardly convex bumps 10a spaced around the inner surface of the shell, near its second or outer perimeter 18 so are to be easily visible to a practitioner. In the embodiment of FIG. 13, the markings are circumferentially spaced holes 10b through the shell, and in FIG. 14 the markings are circumferentially spaced wings 10c on the inner surface of the shell. In the embodiment of FIG. 15, the markings are circumferentially spaced shapes of different types, e.g. triangle, square and rectangle. FIG. 16 has outwardly projecting markings of different shapes and in FIG. 17 and markings are in the form of cutouts or noticed of different shapes. In FIG. 18 the marking is in the form of one or more information containing bar code.

FIGS. 19, 20 and 21 illustrate connecting posts 40 of the invention with lower threaded ends 40a and circumferentially and/or axially spaced projections 40b in FIG. 19, or holes 40c in FIG. 20, or axially spaced rings 40d in FIG. 21. FIG. 22 has rings that are either transverse to the post axis at 40e, or at an acute angle to the axis at 40f or have more than one ring, e.g. crossing rings 40g. Post 40 in FIG. 22 also have a larger diameter stop 40h to positively setting the axial position of the post 40 on the implant 30. This large diameter portion may be just near the threaded portion at the bottom of the post or it may extend part or al the way up the coronal (exposed) portion of the post. FIGS. 23 to 26 illustrate various axially spaced markings types that can be used on the outer end of the post 40 for visual inspection and use with the markings in the shell 10.

Figure 27:
FIGS. 27 to 31 are sectional views of connecting posts of the invention with different shapes.
Figure 26:
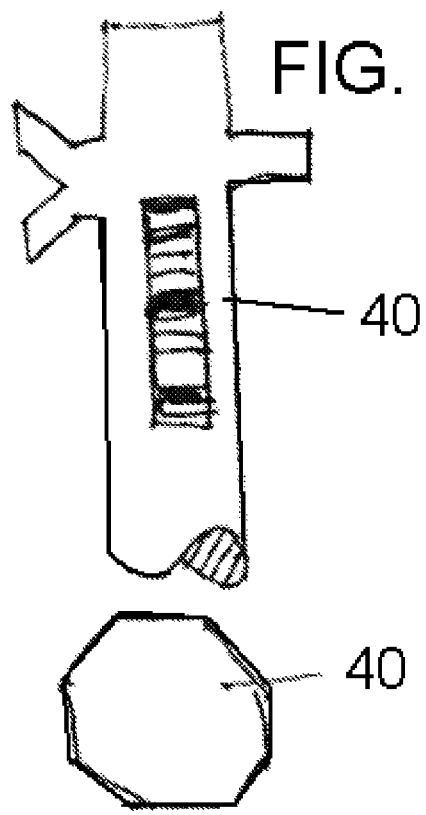
Figure 28:
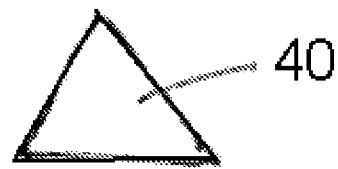
Figure 29:
Figure 30:
Figure 31:
Figure 32:
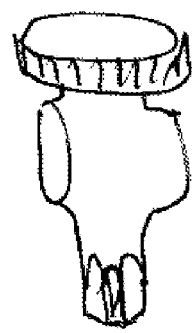
FIG. 32 is a perspective view of a finger-driven or mechanical driver for driving the connecting post of the invention.
Figure 33:
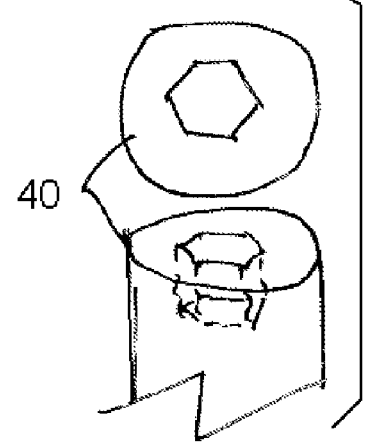
FIGS. 33 to 35 are perspective views of various post drivers provided for driving a post of a complementary cross sectional shape.
Figure 34:
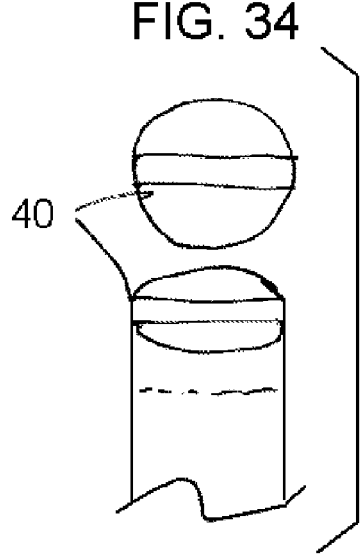
Figure 35:
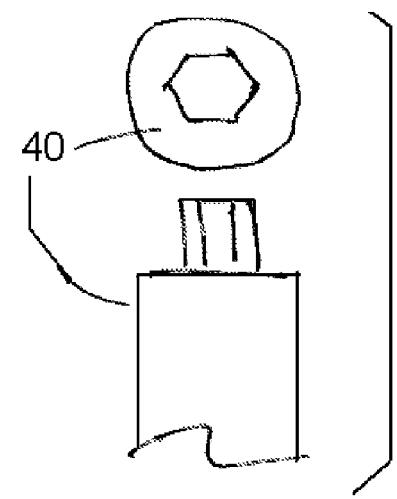
Figure 36:
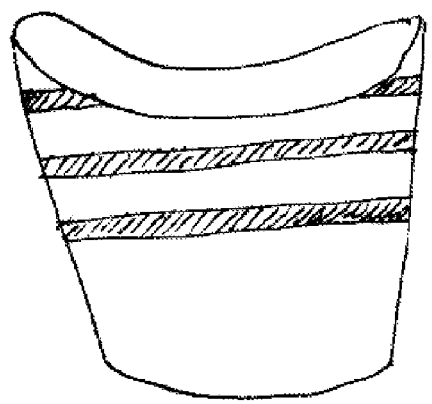
FIG. 36 is a perspective view of a shell 10 with horizontal laser etched lines for use as a measuring gauge to determine the proper depth or height of a transgingival residual soft tissue socket 100 that is left after a tooth extraction so that a properly sized shell can be selected.

To facilitate attaching the post 40 to the implant 30, the post may have a circular cross section as in FIG. 27 that may included an end projections that is non-round like a triangle of FIG. 28, or a hexagon of FIG. 28 or an octagon of FIG. 30 or a rectangle of FIG. 31 making up the entire post or an end projection of the post, that is engaged by a finger or mechanical tool shown in FIG. 32 that had an engagement end with shapes as shown in FIGS. 33 to 35 for screwing the post 40 into the implant 30. FIG. 36 illustrates a sizing shell 10S that has marks in the form of circumferential bands 10d that are axially spaced along the upper outer surface of the shell. In use the practitioner places the sizing shell 10S into the patients soft tissue socket either before or after the connecting post 40 is in place, and observes there the upper margin of the soft tissue socket reaches with respect to the markings. This will give the practitioner a guide to select a shell 10 of proper axial height for the size of the patient's soft tissue socket.

Description of Methods:

It is understood in the description of the method and device that the placement of an immediate soft tissue preservation implant abutment has the intended use for the extraction and replacement of a single tooth or multiple teeth. The method will be described for a single tooth, but it is understood that the deception of the method and device is not limited to a singular tooth but implies a description for multiple teeth as additional embodiments of the invention. FIGS. 6 and 8, illustrate one preferred embodiment of the method of the invention as was detailed above and that results in an immediate temporary abutment or crown, while FIGS. 37 to 45 illustrate another preferred embodiment of the method of the invention that is used to gather image information about the exact angle and depth of the implant as well as the size and orientation of the soft tissue socket. This critical and accurate information can then be used to create a perfectly sized and angles abutment, temporary crown or even a permanent crown that anatomically fits the soft tissue socket while being properly oriented and securely connected to the implant, unlike the prior art that universally forces the soft tissue socket to conform to the idealized abutment that must be axially aligned with the implant while ignoring the actual anatomy of the socket.

Figure 37:
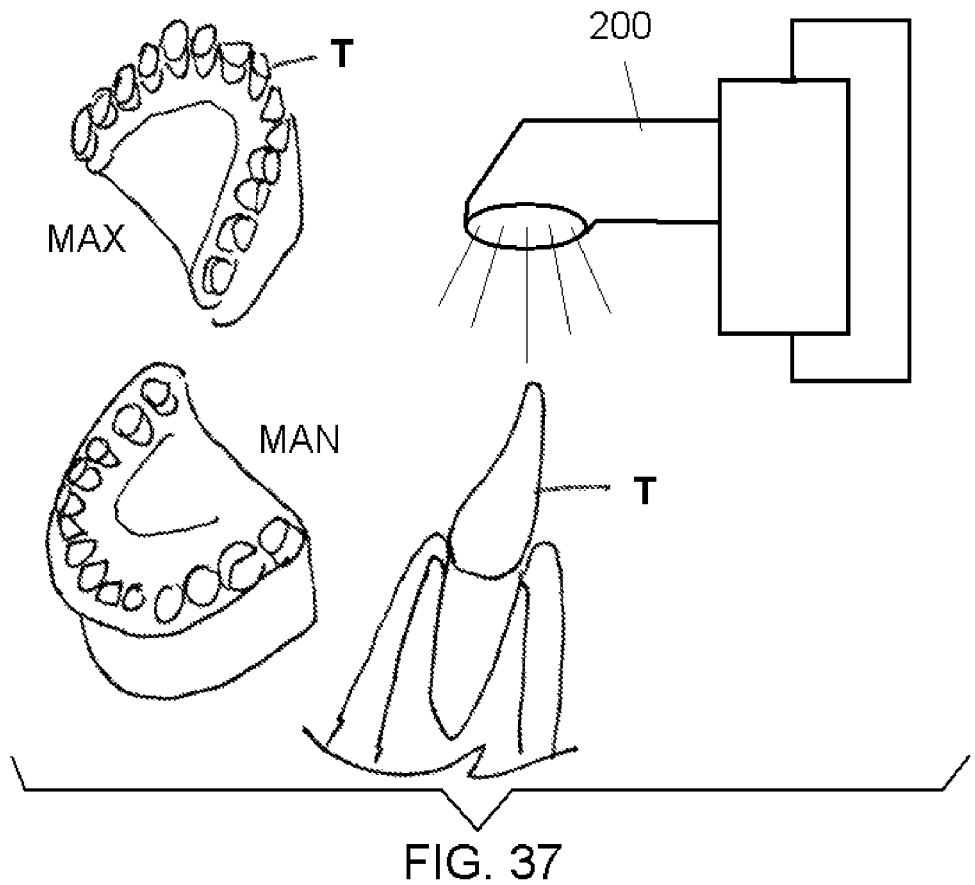
FIG. 37 is a composite illustration of a first scanning step of an embodiment of the invention.

At Step 1 in FIG. 37, the diagnosis that a tooth requires extraction is determined by the dental clinician. The diagnosis is preformed using conventional means including clinical examination, radiographic analysis, detailed past dental history and the review of signs and symptoms. The patient is informed of the treatment alternatives and an appropriate informed consent to treatment is provided to the clinician. During the diagnostic phase a suitable sized hollow shell 10 for the transgingival zone of the residual soft tissue gingival socket can be selected based on dimensional measurements taken from the radiographic records and analysis. A CBCT scan 200 or other means of radiographic studies are suitable for selection of the hollow-shell. It is also possible to select the proper size of the hollow-shell using the sizing hollow-shell 10S with its horizontal laser etched lines 10h to determine the proper depth or height of the transgingival residual soft tissue socket as shown in FIG. 36, but this can only be done after extraction.

Prior to the extraction of the tooth an electronic recording with scanning technology or photographic means is taken to allow future comparison of the pre-treatment condition that was present versus the post-operative outcome after treatment is completed. The image may have a reference measurement tool or instrument so that detailed analysis of the soft tissue changes can be analyzed.

A dental impression is taken either using conventional impression materials such as alginate, polyether, vinyl polysiloxane, or other materials to establish an accurate representation of the teeth and surrounding gingival tissues. It is understood that the described embodiment may also be performed using a digital impression such as laser scanning, photographic imaging, mechanical sensing, cone beam computer tomography or digital oral impression (CAD/CAM Digital Impressions) using a hand-held oral scanning device 200 of known design.

A digital scanning or impression is taken of the maxillary MAX and mandibular MAN arches, including teeth and gingival tissues, in particular including the tooth T to be extracted and the adjacent teeth of the tooth to be extracted.

Figure 38:
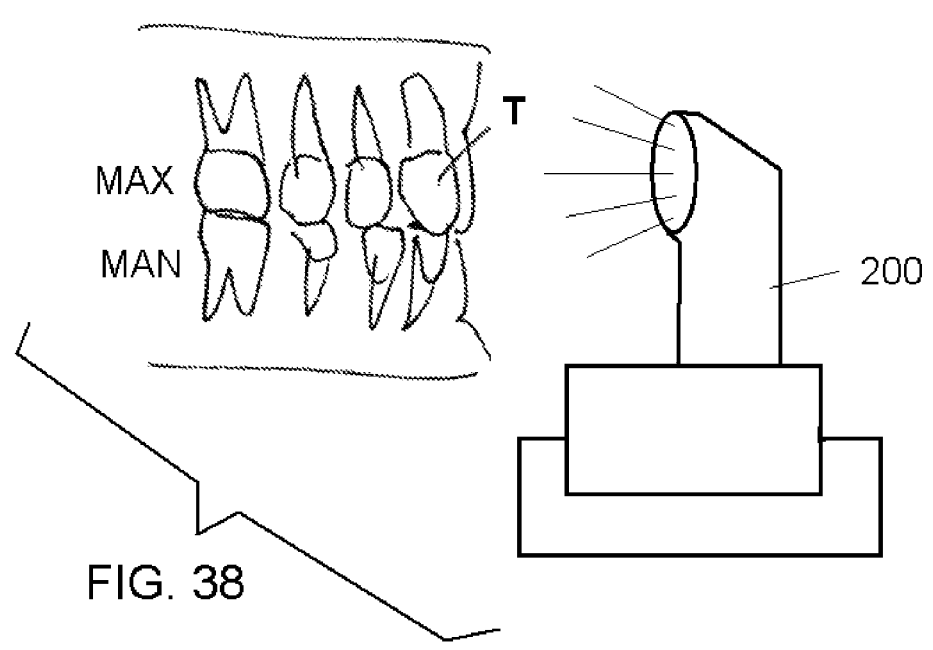
FIG. 38 is a composite illustration of a second scanning step of an embodiment of the invention.

The clinical crown (i.e. the portion of a tooth exposed beyond the gingiva) of the tooth to be extracted is scanned or recorded in FIG. 38, either with electronic means or a physical impression to record the shape, size and topography relative to the adjacent teeth and surrounding gingival tissues. This is done with the patient's jaw closed so that this occlusion scanned information can be spatially referenced to the position of the residual soft tissue gingival socket once using the hollow shell with orientation markings once the tooth is extracted and a bite record is also made. This dimensional information is used in the fabrication of the dental implant prosthesis components.

A digital scanning or bite registration of the opposing teeth is thus recorded in Step 2 of FIG. 38 with either an electronic scanning technique or a physical bite registration material. The occlusal surface contact to the clinical crown of the anticipated extracted tooth is recorded to record the spatial relationship of the teeth to the position of the residual soft tissue gingival socket. This dimensional information is used in the fabrication of the dental implant prosthesis components. The opposing arch contact to the tooth to be extracted is recorded to enable the opposing contacts of occlusion to be established in the laboratory model to be used for fabrication of the components of an implant restoration.

Figure 39:
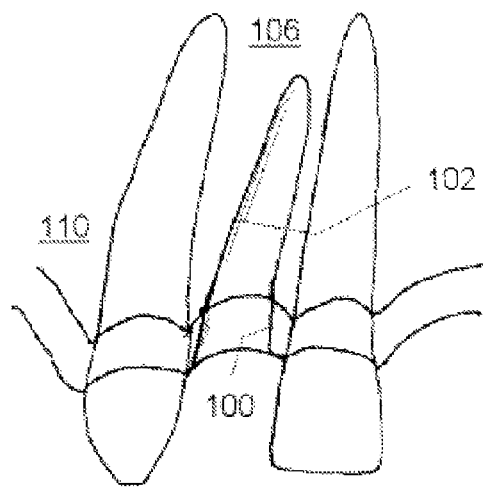
FIG. 39 is an illustration of a third extraction step of an embodiment of the invention.

In Step 3 of FIG. 39, the area of the mouth in which the tooth T is to be extracted is anesthetized with a dental local anesthetic solution. A local anesthetic solution can be delivered to the area either as local infiltration dental injection or as a regional nerve block to the area. The patient is given adequate time (typically 5 minutes) for the dental local anesthetic to anesthetize the region of the mouth that is being treated.

Extreme care is used to preserve the entire tissue-zone and minimize trauma to the supporting gingival tissues 106 during each phase of treatment. It is critical to preserve the soft tissue architecture or socket 100 of the immediate and surrounding gingival in order to re-establish the biologic-seal after the tooth is removed and the immediate soft tissue implant abutment, i.e. shell 10, is placed. Therefore a flapless surgical technique is used.

The next Step 3 to performing the method of the invention is to carefully incise the entire supra-crestal attachment of the tooth to be extracted, 360 degrees around the tooth, i.e. around soft tissue socket 100. It is important to surgically disconnect the soft tissue attachment fibers. This can be accomplished using a surgical blade, piezo-surgical instrument, micro-rotary dental handpiece or dental laser soft tissue cutting instrument. The method requires careful dissection of the supra-crestal attachment which includes the sucular epithelium, junctional epithelium, and the connective tissue inserting fibers which are found between the connective tissue and the surface of the root above the crest of bone. Once the supra-crestal fibers are released the superior periodontal ligament fibers (attachment fibers found between the alveolar bone socket and root surface) can next be incised.

The superior periodontal fibers attach the surface of the tooth (cementum) to the inner bony socket must also be severed using minimal disruption to the surrounding soft tissue and bony architecture. This can be accomplished by using micro-surgical instruments, periotomes, a rotary diamond pointed diamond, piezeo-surgical instrument, laser. It is important that the instrument diameter is between approximately 20 microns to 50 microns (or ⅛ to ¼ millimeter in diameter) as this is the dimension of the width of the periodontal ligament space. The surgical instrument is placed into the entrance of the periodontal ligament between the tooth 104 and inner socket wall 100. The periodontal attachment fibers are served around the tooth to a depth of 1 to 4 millimeters, depending on ease of entry into the periodontal ligament space.

The extraction of the tooth is first initiated using a rotational movement in order to sever the remaining subcrestal periodontal fibers attaching the tooth to the inner socket wall. This can be performed with either using a reduced diameter elevator, periotome or extraction forceps. Once a rotational movement is achieved a vertical force can be applied to the tooth to advance the root out of the bony socket 102.

When the extraction is performed using this method minimal disruption can occur to the surrounding soft tissues 106 of the gingival. The interdental papillae are not surgically altered from the pre-treatment condition. Incisors are not made which compromise the blood supply to the region of the bone or surrounding soft tissue gingival. The architecture of the soft tissue has not be altered other than the severing of the attachment fibers between the root surface and inserting fibers.

As part of Step 3, removal of any inflammatory granulation tissue within the bony socket 102 may be necessary. This is performed using a small sized circular curette. Inspection is performed to ensure the integrity of the remaining inner socket walls 100. A radiograph may be taken to determine the remaining configuration of the tooth socket. This step is referred to here as preparing the bony or bone socket.

Figure 40:
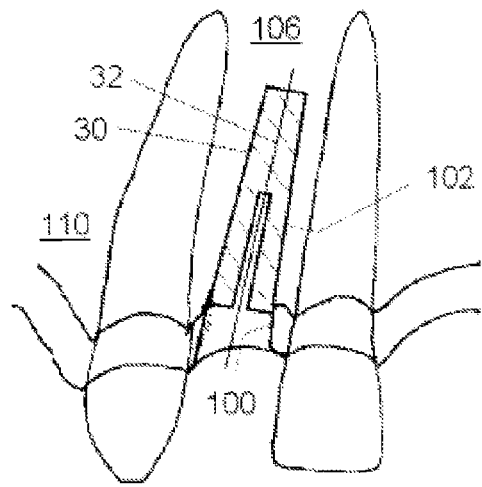
FIG. 40 is an illustration of a fourth immediate implant placement step of an embodiment of the invention.

After the boney socket 102 is prepared following known dental procedures, immediate insertion of dental implant 30 is performed in Step 4 as illustrated in FIG. 40. A dental implant 30 is immediately placed within the residual extraction socket 102. The term "immediately" as used here means that the implant is placed shortly after the bony socket has been fully prepared to receive the implant, 10 to 30 minutes for example, but importantly during the same patient's visit.

The vertical position of the implant is established. The implant 30 can be placed at the level of the remaining crest of bone 110. Since the remaining crest of bone has different heights the implant may be slightly supra-crestal as one region and slightly subcrestal at another region of the socket, this is to be expected.

The horizontal position of the implant is established. The implant 30 is to be ideally placed with the implant axis 32, axial position allowing for a screw-retained temporary. The center axis of the implant 32 must therefore be placed in the position of the root socket 102 to engaging a maximum volume of remaining bone. The implant is positioned toward the palatal (lingual) aspect of the residual extraction socket 102 when possible. It is noted that the implant 30 will not be placed in the center of the socket 102 as this would result in the retention screw of the immediate-temporary to exit through the incisal edge of the tooth and will result in an esthetic compromise of the restoration. Positioning the implant biased toward the palatal (lingual) position of the extraction socket is critical so that a screw-retained immediate temporary restoration can be used. This advantageous placement of the implant is made possible by the fact that the abutment or shell 10 of the invention is independently positioned relative to the implant and need not be affixed with respect to the axis or position of the implant as has always been the case in the past. The preferred embodiment of the invention is an immediate screw-retained temporary to eliminate the need for cementation of the temporary. Retention of the immediate temporary relies upon mechanical retention of the screw. It is anticipated that the immediate temporary could be designed in with a temporary design in which it is cemented to the substructure directly and places the location of the gap below the soft tissue zone.

It is also noted that the soft tissue axis 12 of soft tissue socket 100, will rarely be coaxial with the implant axis 32 as shown in FIGS. 10, 11 and 40 and it is the ability of the present invention to accommodate this anatomical reality without forcing a deformation upon the soft tissue socket 100, by independently positioning the shell 10 with respect to the implant 30, that most drastically distinguishes the present invention from the prior art.

The immediate implant 30 must mechanically engage and lock into a portion of the remaining bone. This may be achieved at the apical end of the implant. It may also be achieved on a lateral portion of the surface of the implant.

It is understood that the implant diameter will be smaller then the greatest diameter of the root of the tooth that was removed. Therefore the dissimilar diameters between the immediate implant and the residual bony tooth socket must result in a lateral "gap" or space between the residual bony socket 102 and the surface of the implant 30 as shown, for example in FIG. 6. Filling the entire tooth socket 102 is not desirable, as this method relies upon a residual gap between the facial surface of the immediate implant and the remaining buccal plate of bone. This gap will then allow for the placement of a bone regenerative material to be placed between the implant surface and the inner tooth socket buccal plate. The gap allows for future bone regeneration via the in growth of the blood supply and new osteoblasts. It is important not to use a implant diameter that would make direct contact to the labial plate of bone as this would compromise the blood supply that is needed to preserve the labial (buccal) plate of bone as the implant surface provide no ability for angiogenesis. This is critical point to appreciate and understand. The preservation of the overlying gingival and surrounding soft tissues is preserved by several critical factors: (1) a minimally invasive surgical approach; (2) preservation soft tissue architecture; and (3) preservation and promotion to re-establish the blood supply to the surrounding tissues.

Figure 41:
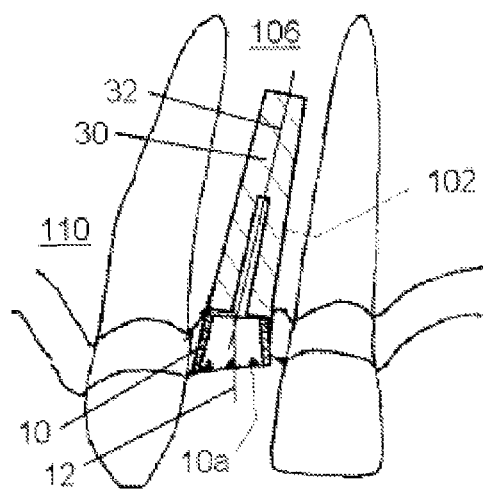
FIG. 41 is an illustration of a fifth hollow shell placement step of an embodiment of the invention.

FIG. 41 shows how a marked version of shell 10 is used during Step 5, as a first orientation component. Hollow shell 10 that has been selected to best fit the soft tissue socket 100 which at this early time after extraction has not collapsed or become overly deformed is now placed in socket 100 during Step 5. Placement of the hollow shell with orientation and dimensional information markings 10a or 10b or 10c (see FIGS. 12-18), is fitted into the residual soft tissue gingival socket 100 so that a contact is made between the entire perimeter and the internal surface of the soft tissue socket as previously described. The hollow shell with distinct visual or physical markings provides orientation and shape and size of the socket may be performed.

Figure 42:
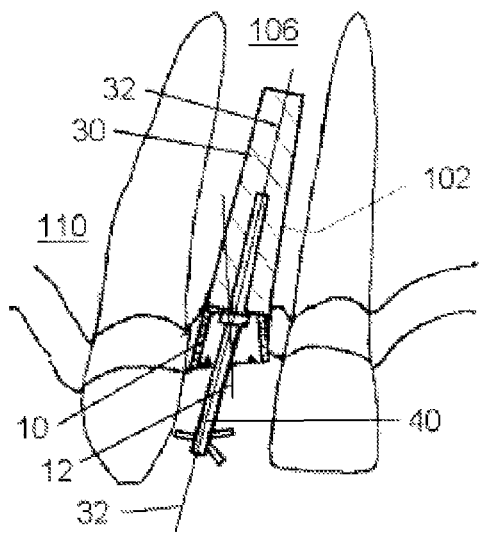
FIG. 42 is an illustration of a sixth connection post placement step of an embodiment of the invention.
Figure 43:
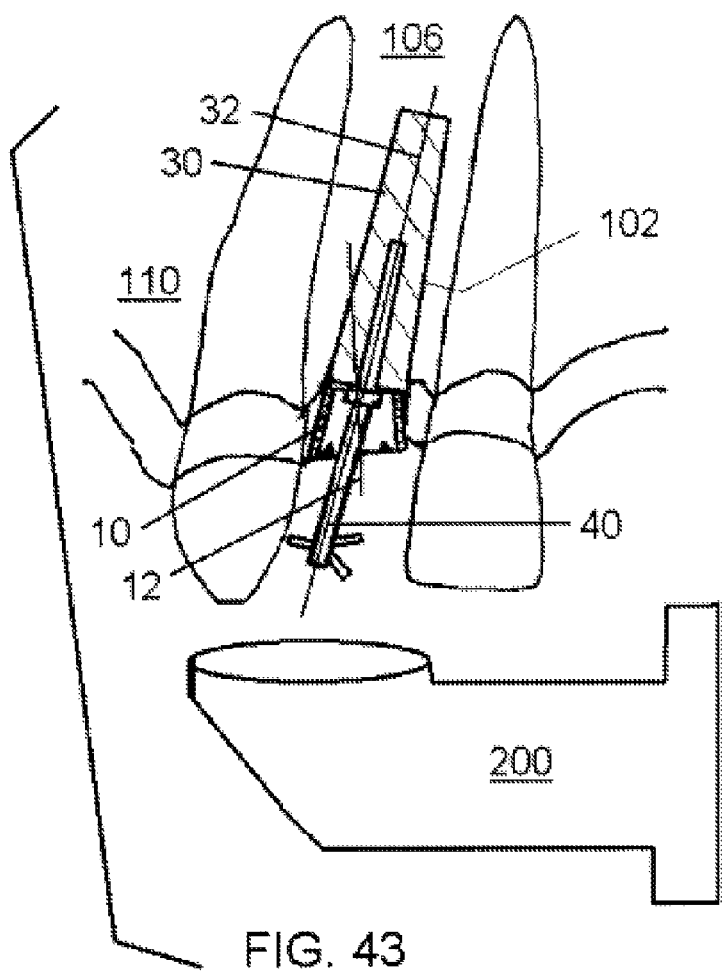
FIG. 43 is an illustration of a seventh scanning step of an embodiment of the invention.

Step 6 illustrated in FIG. 42 can actually occur before Step 5 but it may be more convenient to execute the shell placement Step 5 before the second orientation component in the form of the temporary, connecting post 40 is placed. The connection post 40 is affixed into the root-form implant 30 by having its lower threaded end 40a screwed into the threaded hole in implant 30 as shown in FIG. 42. The first component (shell 10) and second component (post 40) are separate and do not make physical contact so that the second component does not influence the position of the first component in any way.

This independent positioning is further insured by the requirement that the minimum inside diameter of shell 10 always be greater than the maximum outside diameter of post 40. This relation is also true for the embodiment of FIGS. 1-8, that includes a separate securing screw 50 to secure the normally larger diameter post 40 that is designed for use with luting compound.

The spatial relation of the two independent and marked components 10 and 40 in FIG. 42 is recorded as noted above as part of Step 7 illustrated in FIG. 43. That is, the position of these two components is recorded by means previously discussed using scanning 200 or physical dental impressions to fabricate an electronic model or a laboratory dental model. The model (electronic or physical) can then related and indexed to the pre-treatment models previously taken. The models provide the x, y, z spatial coordinates of the residual soft tissue gingival socket related to the other dental components described including the clinical crown and the contacts of the adjacent and opposing teeth of the extracted tooth.

The connection post 40 is selected for the proper vertical height so that the connection post extends beyond the coronal surface of the hollow shell 10. The connection post can be screwed retained or mechanically retained by a frictional interference into the internal threaded portion of the root-form implant 30. A vertical stop 40h on the connection post 40 (see FIG. 22) will define a vertical relationship of the post and root form implant 30 relative to the hollow shell 10 and residual soft tissue gingival socket 100. Distinct markings on the connection post coronal section provide the orientation, vertical, horizontal and transverse of the position and dimensional specifications of the connection post. The connection post directly provides the spatial position of the root-form implant contained within the bone relative to the residual soft tissue gingival socket.

Figure 44:
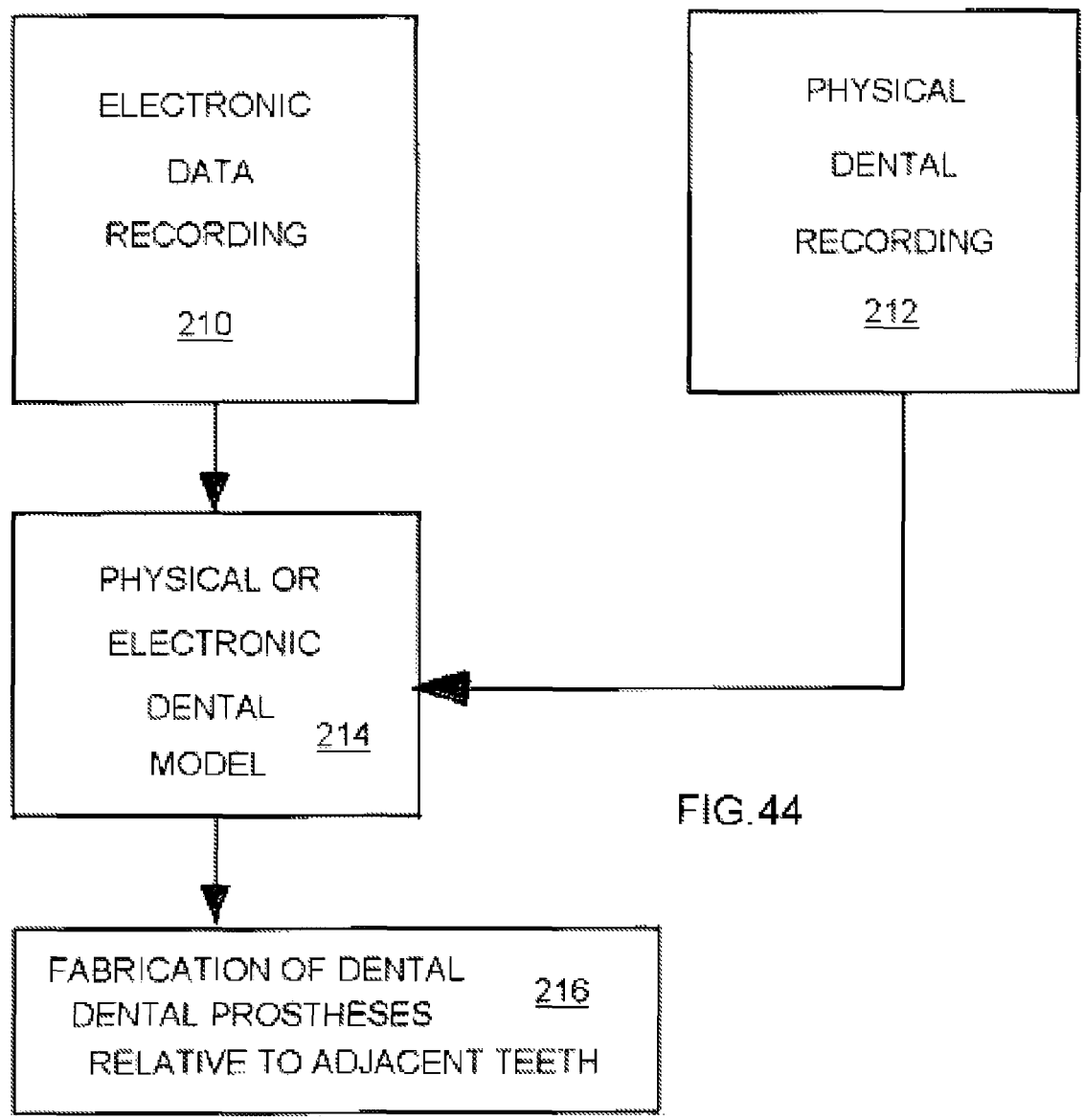
FIG. 44 is an illustration of an eighth data processing step of an embodiment of the invention.

FIG. 44 illustrates the sequence of electronic data recoding via image scanning at step 210 or dental impressions at step 212, with the data or impression used for physical or electronic dental modeling in step 214, followed by fabrication in step 216.

In all embodiments of the invention the connection post 40 and the hollow shell 10 are independent from one another so that neither component influences the position of the other. Non-centric positioning of the implant relative to the hollow shell can be recorded by use of individual components. Acute angles between the position of the residual soft tissue gingival socket and the root-form implant can be obtained from the two separate components placed independently.

Figure 45:
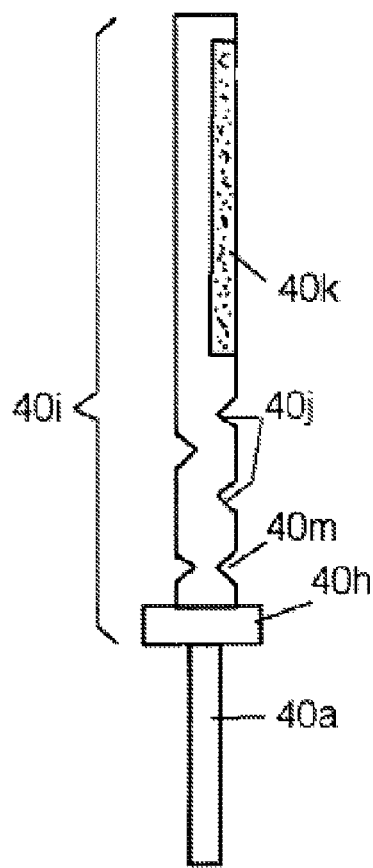
FIG. 45 is a side view of a connection post of the invention with a breakaway feature.

As shown in FIG. 45, the connection post coronal section 40i may be designed with undercuts 40j or a roughened surface 40k to allow materials to be attached to the surface at a later time. A breakaway cut or weakened area 40m may also be provided to allow for a defined breaking location incase excess lateral force or torque is applied to the post 40, so that an accessible portion of post 40 remained above the implant 30, so that the remaining post portion can be removed form the implant.

The connection post 40 may be used as a means to retain the hollow shell 10 during the fabrication of a temporary or a screw-retained temporary post may be inserted into the root-implant, e.g. to form part of the temporary abutment.

Fabricating the Temporary Abutment:

Returning to the embodiment of FIGS. 1-8, the screw-retained temporary post 40 is connected by screw 50 to the dental implant 30 that in turn is held within the boney socket 102.

The immediate soft tissue abutment shell 10 is selected for the proper vertical and horizontal dimensions either by eye or using the sizing shell 10S. The immediate soft tissue preservation abutment shell 10, as noted above, is supplied in different dimensions depending upon the tooth to be replaced. It will have series of defined dimensions externally. These dimensions will include a series of different tissue-zone heights ranging from 2 mm to 5 mm. It will be provided in several root form configurations and be provided in more then one horizontal widths. An example of the horizontal dimensions could be, but not limited to:

Maxillary Right Central Incisor: Height 2 mm, Height 3 mm, thru 5 mm. Diameter, Small, Medium and Large. An irregular superior surface is provided to conform to the soft tissue gingival architecture. The interproximal points will be longer in dimension then the labial and lingual surfaces. The inner shell allows for the eccentric position of the shell over the center axis of the implant held within the bone.

Maxillary Right Lateral Central Incisor: Height 2 mm, Height 3 mm, thru 5 mm. Diameter, Small, Medium and Large. An irregular superior surface is provided to conform to the soft tissue gingival architecture. The interproximal points will be longer in dimensions then the labial and lingual surfaces. The inner shell allows for the eccentric position of the shell over the center axis of the implant held within the bone.

Maxillary Right Canine: Height 2 mm, Height 3 mm, thru 5 mm. Diameter, Small, Medium and Large. An irregular superior surface is provided to conform to the soft tissue gingival architecture. The interproximal points will be longer in dimensions then the labial and lingual surfaces. The inner shell allows for the eccentric position of the shell over the center axis of the implant held within the bone.

Maxillary Left Central Incisor: Height 2 mm, Height 3 mm, thru 5 mm. Diameter, Small, Medium and Large. An irregular superior surface is provided to conform to the soft tissue gingival architecture. The interproximal points will be longer in dimensions then the labial and lingual surfaces. The inner shell allows for the eccentric position of the shell over the center axis of the implant held within the bone.

Maxillary Left Lateral Central Incisor: Height 2 mm, Height 3 mm, thru 5 mm. Diameter, Small, Medium and Large. An irregular superior surface is provided to conform to the soft tissue gingival architecture. The interproximal points will be longer in dimensions then the labial and lingual surfaces. The inner shell allows for the eccentric position of the shell over the center axis of the implant held within the bone.

Maxillary Left Canine: Height 2 mm, Height 3 mm, thru 5 mm. Diameter, Small, Medium and Large. An irregular superior surface is provided to conform to the soft tissue gingival architecture. The interproximal points will be longer in dimensions then the labial and lingual surfaces. The inner shell allows for the eccentric position of the shell over the center axis of the implant held within the bone.

It is understood that each shells 10 can be for the specific tooth being replaced. The dimensions of the shell are based on measurements of numerous soft tissue sockets remaining after tooth removal. The shell 10 has the requirement to enable a soft tissue socket-seal to be re-established. This is predicated upon allowing the proper dimensions to completely fill the soft tissue (tissue-zone) socket 100.

In general terms and from observation of stone casts and extracted teeth as well as descriptions, pictures and illustrations in Dental Anatomy book, it seems that the "lingual valleys" are lower than "facial valleys" in maxillary and mandibular incisors. Max. and mand. canines "valleys" are of about equal height. Max. and mand. premolars and molars seem the opposite of incisors where "lingual valleys" are higher than "facial valleys" and mesial and distal peeks are not as highly scalloped as in incisors. Of course there are always exceptions and slight variations to the rule since each person dental anatomy will vary.

These rules hold for a shell such as in FIGS. 1 to 8 for fabricating an immediate abutment, and for the marked shells of FIGS. 9 to 45.

The preferred embodiment of the hollow shell with orientation and dimensional markings and the immediate soft tissue implant preservation abutment shell is generally defined as a "tubular shell" which is open at both ends at perimeters 16 and 18. The inferior is placed into the soft tissue socket 100 which does not make direct contact with the implant head platform of the implant 30 within bone 106. The superior surface is to approximate the free-gingival margin of the surrounding tissue-zone. The outer surface of the shell 10 is to make direct contact with the inner soft tissue residual socket 100. The final adapted shell eliminates all openings and gaps between the soft tissue socket and surrounding gingival. This re-establishes a biologic-seal to the underlying tissues below the surface. This will also provide containment and protection of any bone regenerative materials that are placed between the surface of the bone socket and the surface of the implant filling the "gap" between the dissimilar diameters of these two structures.

The hollow marked shell 10 has one or more orientation markings on the occlusal surface of the hollow shell as seen FIGS. 12 to 18. The markings may be indents, detents, wings, tabs, laser etched markings, decals or the use of a single bar code can be used separate or in combination to the markings described. The markings provide the spatial orientation of the shell positioned within the residual soft tissue gingival socket. These "markings" can be detected by electronic scanning means or provide adequate physical identification that they can be recorded using an impression material commonly used in dentistry such as polyether impressions, alginate impressions, rubber base impressions and the like.

The preferred embodiment of marked connection post 40 with orientation and dimensional markings of FIGS. 19 to 35 and 45 that is affixed to a root-from dental implant 30 is generally defined as a single post with three sections; coronal section, vertical stop section and implant engagement section. The coronal section displaying unique markings represented by indents, detents, wings, tabs, decals, laser etching, holes as well as a bar code label. The cross-sectional geometry of the coronal section may be round, triangular, hexagon but not limited to these shapes. A shape may be selected to allow a mechanical driver to be attached to the top for placement and removal. The coronal aspect of the connection post can be designed with a groove or internal hex or opening to allow a transfer of the connection post using a finger or mechanical driver. The coronal section of the connection post may be smooth surfaced, roughened or designed with undercuts that are staggered or circumferential. The surface pattern may be designed to allow the adhesion of a material or materials. It is understood that materials that adhere to the surface could be become dislodged upon insertion and removal of the connection post from the root-form implant. This would facilitate using the connection post in combination with a temporary abutment. It is also possible that an external sleeve is applied to the outer surface in a coaxial design to which materials can adhere to. The coronal section of the connection post may be designed with a stress-breaker feature so that if the connection post exhibits overloading be it functional or mechanical the connection post will separate at a pre-defined location. The stress-breaker feature would prevent damage or blockage of the root-form implant access hole by breakage of the connection post at the level of the head of the root-form implant platform.

The vertical-stop section of the connection post is designed as mechanical interference when inserting the post within the root-form implant. This vertical-stop creates a defined length from the head of the implant platform to position of the unique markings enabling the spatial positioning of the root-form implant to be related or indexed to the residual soft tissue gingival socket position. The shape of the vertical-stop may be round, hexagon, octagonal, slotted or other geometric shape. The shape allows an instrument to engage the surface for removal of the connection post from the root-form implant. The vertical-stop may also be represented by a transition in the surface between threaded and non-threaded or a transition between different diameters to the width of the connection post.

The engagement section of the connection post is designed to provide a stable fit within a root-form dental implant. This may be fixed to the dental implant via internal screw, frictional interference or other means of active fit between the connection post and the root-form implant.

In the preferred embodiment electronic impression using a hand-held scanning device which records the distinct markings and orientation of the hollow-shell relative to the dental implant connection post is performed. In an alternative embodiment impression are taken using physical impression materials recording the markings on the hollow shell, dental implant connection post and surroundings tissues. This information can be used to fabricate a variety of implant prosthetic components to be used for the temporization and final fabrication of the final implant prosthesis, including but not limited to the abutment, crown, monolithic abutment/crown restoration and/or a variety of components to accommodate the placement of final restoration. It is possible to achieve this without luting the two components of the hollow shell and the implant post connection. In one embodiment that patient stays in the office as a custom abutment is fabricated by transferring the digital information to electronic Additive or Subtractive dental fabrication machines, examples included but not limited to CAD/CAD Milling machine, 3D printing, Stereolithographic, 3-D inkjet technology that can immediately or rapidly fabricate a temporary abutment from a variety of acceptable dental materials.

In another embodiment a pre-treatment electronic or physical dental impressions is taken to relate the surrounding teeth and gingival to the prosthesis to be fabricated. It is also possible to take a pre-scan or pre-op impression so that the replication of the clinical crown of the tooth removed can be electronically or physically available for the fabrication of the prosthesis and its components. It is anticipated that that final monolithic prosthesis or multi-component prosthesis can be fabricated that includes the abutment and the clinical crown fabricate from a suitable dental material, examples include, but limited to, zirconium oxide ceramic, resin or resin-ionomer, polymethyl methacrylate (PMMA), polyetheretherketone (PEEK), lithium disilicate, or zirconium dioxide, ceramic of other durable material such as gold alloy, e.g. AuPdAg (gold-palladium-silver). An access screw hole is provided within the restorations for retention of the process directly to the dental implant.

In yet another embodiment the fabrication of multiple components such as a custom abutment that is screwed to the head of the dental implant is fabricated. The abutment allows the cementation of a clinical temporary that can be fabricated at the chair side at the time of the surgery. What is of critical importance is the ability to capture that anatomic and spatial relationship of the residual soft tissue socket of the fresh tooth extraction site using a hollow shell with orientation and shape and size markings. This can be spatially related to the underlying immediate root-form implant through the use of a connection post with orientation and shape/size markings. This can be accomplished in spite of the relative position of these two critical structures. Additionally, recording the relationship of the residual anatomy of the soft tissue gingival socket does not require physical contact of the hollow shell to the underlying dental implant, nor does it require the physical contact to the dental implant post to capture and provide this information in the fabrication of the prosthetic components.

The prosthetic components that are fabricated from the recordings of the spatial relationship of hollow shell and dental root form implant can placed. Removal of both the hollow shell and the dental implant connection post is performed. An immediately fabricated abutment is placed into the patient mouth and secured (screw retained or cemented) to the underlying immediate dental implant. The custom abutment provides proper soft tissue seal and protection of the underlying residual soft tissue socket. Yet another embodiment would allow the fabrication of a temporary clinical crown to be attached to the intervening custom abutment that has been fabricated. Adequate time for osseo-intregration of the dental implant is allowed.

In yet another embodiment the hollow shell with orientation markings and the connection post markings is used to record the spatial relation of the residual soft tissue gingival socket to the underlying root-form implant. The relationship is recorded by the means previously described. Fabrication of prosthesis components can be initiated. It is also anticipated that the surgeon may elect to record the relationship of the soft tissue socket to the underlying root-form implant and then place a conventional healing cap affixed to the dental implant. The soft tissue would heal without further consideration. The recorded relationship could be used to fabricate an abutment and or abutment and final prosthesis and be placed at a later date. The advantage to this is approach capturing the soft tissue anatomy prior to changes that are typically seen during healing. At a subsequent time the fabricated prosthesis components can be placed to re-establish the soft tissue contours to the state prior to the removal of the tooth at that site. This enables a customized abutment to be fabricated and be placed with a delayed approach for the immediate implant placement into a fresh extraction site.

The electronic data recordings described provide information that is transferred to the fabrication of a physical or electronic model (3-D CAD model as an example). These models then to serve to allow the fabrication of components that are to be used for dental implant prosthesis. The components to be fabricated include, but are not limited to, implant abutment, implant crown, one piece monolithic implant abutment-crown. The fabrication of the dental implant prosthesis components can be fabricated by CAD/CAM, additive or subtractive automated digitally machines, digital CAD milling machines and the like.

Once the hollow-shell with markings and the connection post with markings is used to record the spatial relationship of the residual soft tissue gingival socket these components can be used to fabricate a temporary prosthesis as previously described. It is also possible that these components are removed and the placement of other temporary abutment components is used.

Additionally, a membrane can be placed at the level of the bony crest and placement of the shell 10 will provide complete coverage of the membrane below providing a biologic-seal to the outer oral environment. Once the shell is filled (the luting step) and modified it will also provide structural support to the soft tissue gingival to prevent and preserve the architecture. The surface of the immediate abutment shell promotes soft tissue adhesion to the surface. Allowing the superficial layers of the dermis to adhere to a smooth superior region of the abutment shell as well as encouraging functional fiber orientation to the roughened inferior region to promote a functional connective tissue attachment.

Luting (chair-side connection) of the immediate soft tissue implant preservation abutment shell to the retaining screw-post of the implant: Once the proper abutment shell is selected from the variety of sizes and diameters it is placed within the tissue-zone soft tissue socket. It is eccentrically positioned to the implant as previously described so that the outer surface of the shell make physical contact ensuring a biologic-seal between soft tissue and surface of the shell. It is luted or connected to the screw-post in this position by using a chair-side technique. The technique of connecting the shell 10 to the screw-post 40 can be performed with a variety of materials 60, in the preferred embodiment a cold-cure acrylic is used, in additional embodiments any number of polymerization materials can be used but not limited to composite, acrylic, resin, etc. The entire internal surface of the shell 10 is filled with luting compound as shown in FIGS. 6 and 8, eliminating voids or gaps within the material.

The superior surface can be filled to the level of the free gingival margin. An access hole will remain to allow removal of the shell, e.g. but inserting a nylon plug 80 into the central hole of the post 40 as shown in FIG. 8, for final finishing and temporary insertion.

The inferior surface is modified and any gap or voids are filled chair-side and then re-surfaced as described below.

Re-surfacing of the shell material, preparation and handling: In certain situations it may be necessary to modify the shape and surface of the shell 10 to properly adapt to the soft tissue socket 100. An additive technique of material or subtractive technique can be required in which additional materials or added or removed. To resurface the modified outer shell a novel surface texture bur is attached to a standard rotary handpiece. This preservation abutment shell bur is designed to re-establish the surface texture that was created in the texture zone on the outer surface of the abutment shell. A second step of cleaning is then required to ensure removal of all contaminants. This second surface cleaning step is accomplished by thorough cleaning, in the preferred embodiment this can require high-pressure, high-heat steam cleaning in alternative embodiments it is anticipated that autoclave, antimicrobial cleaning solutions may be applied to the surface to detoxify the contaminated surface.

After filling and reshaping of the shell 10 is completed it is removed from the implant by un-screwing the retaining screw 50. The abutment shell is then cleaned and inspected and all voids are filled and re-surfaced and cleaned as described above.

Placement of a standard cylindrical healing abutment is attached to the plate-form. The standard cylindrical healing abutment may be composed of titanium, stainless steel, anodized metal or other metal. It is conceivable that the standard cylindrical healing abutment is made from a cost saving polymer and disposed of after removal as this component is to be used as an intra-operative space maintaining during the placement of bone regenerative materials during this method. The standard healing abutment is selected to attach to the implant resulting with a noticeable gap between the outer surface of the standard cylindrical healing abutment and the soft tissue socket. Bone grafting materials are placed within the gap between the bony socket 102 and surface of the implant 30 at or below the crest of bone. An optional barrier membrane can be positioned if necessary before or after the bone grafting materials being put into placed.

The standard cylindrical healing abutment is removed and discarded and the contoured refinished abutment inserted. In the preferred embodiment the retaining screw is put into placed and applying a seating torque to the screw that is between 15 newton-centimeters to 35 newton-centimeters.

The abutment shell 10 is adjusted to ensure that it is not in occlusal contact with the opposing teeth 104 when the patient closes their mouth.

A final radiograph is taken to assess the fit and position of the implant and shell.

The abutment shell 10 creates a biologic-seal to the underlying soft tissue and preserve the integrity of the surrounding gingival architecture. The abutment shell 10 is not to be removed for a minimum of 3-4 months at which time the fabrication of the final prosthesis can be initiated.

Further Structural Details of the Invention:

As noted, illustrated and described above, abutment shell 10 in its preferred form, is generally a tubular shell which is open at both ends. The tubular shell has the following specifications but it is anticipated that it may also have other designs features:

The shell is an irregular tubular design that mimics the shape of residual soft tissue (tissue-zone) socket 102 that remains after a tooth has been removed. Examples of these shapes (generally occlusal views) are provided in FIGS. 2-5. The shape may more closely mimic the cross-sectional outline of a root in the tissue-zone region, but may also be designed to over-compensate on one or more surfaces to ensure physical contact along all aspects of the soft tissue tooth socket. It is critical that the shell's fit with contact and not be causes excessive contact pressure at any specific point or area of the soft tissue socket.

Design of Markings of Hollow Shell and Connecting Post

Outline shape of the two ends of the preservation abutment shell 10 is irregular as also illustrated in the drawings. The superior (gingival) surface of the shell (at outer perimeter 18) has a larger area when compared to the inferior (implant) surface (at inner perimeter 16) that comes into contact with the platform head of the implant 30.

The vertical height of the tubular shell will not be uniform. The interproximal surfaces at peaks 20 and 22 have a greater height when compared to the buccal and lingual surfaces at 24 and 26 of the tubular shell 10.

The emergence profile of the shell is one that has a variety of profiles to compensate for the position of the implant within the residual socket. Since the implant is to be intentionally placed off-center from the extracted tooth, the shell is intentionally placed eccentric to the immediate implant 30, placed within the bone. The shell is designed to be placed eccentric to the implant head. The emergence profile of the shell is over-compensated and under-compensated in the profile design allowing for the position of the implant. The compensating emergence profile design and ability to place the shell eccentric enables the re-establishment of an effective biologic-seal between the outer surface of the shell and the residual soft tissue perimeter. The shell can be confined to the transmucosal (tissue-zone) region extending from the crest of bone to the free gingival margin or it may continue to extend into the oral cavity as the labial surface of material to replace the labial surface of the removed tooth in addition to the transmucosal region.

Surface Texture of Shell—In the preferred embodiment the outer surface text design can possess two distinct surface texture regions. The superior (gingival) surface region can be smooth to discourage the accumulation of plaque. The superior smooth zone may extend 1 mm to 3 mm. The inferior region will possess an ordered microgeometric repetitive surface texture or pattern. The inferior textured region covers the remaining outer surface. This textured surface encourages the re-establishment of the gingival fibers to make contact and adhere to the surface of the temporary abutment. The surface texture is not limited to two or more texture patterns, it is conceivable that the surface of the shell be design with a single texture covering the entire surface or designed from multiple textures to encourage direct soft tissue adaptation within the tissue-zone. A smooth surface at the superior regions discourages plaque accumulation while the textured surface promotes and accelerates effective soft tissue adhesion. The surface design discussed in the preferred embodiment has been shown to promote soft tissue preservation in combination with providing an effective biologic-seal of the surface of the shell to the residual soft tissues.

The hollow shell with distinct identification and orientation indications or markings upon the hollow shell as shown in FIG. 12-18. The markings may be of a design of physical markings, such as holes, grooves, geometric spaces, indents, detents, internal or external tabs or wings and/or visual markings, laser etching, decals, colored markings or other means of recording spatial orientation of the hollow shell and it's relationship to the residual soft gingival socket. The markings will also code for the physical shape and dimensions of the hollow shell selected for use.

The connection post 40 for the root-form dental implant (FIGS. 19-35) with distinct identification and orientation indications upon the connection post. The markings may be of a design of physical markings, such as holes, grooves, geometric spaces, indents, detents, internal or external tabs or wings and/or visual markings, laser etching, decals, colored markings or other means of recording spatial orientation of the connection post and its relationship to the root-form dental implant. The markings will also code for the physical shape and dimensions of the connection post selected for use. The connection post may be retained by a variety of means including but not limited to screw, frictional interface, etc.

The shell can be composed of a variety of biocompatible materials including but not limited to; ceramic, acrylic, porcelain, lithium disilicate, zirconia and other crystalline structure. It is anticipated that this material can be composed of materials that are anti-microbial, bacteriostatic to retard the growth or colonization of the surface and internal surfaces with micro-organisms. Examples of such materials include but are not limited to; silver, copper, magnesium, titanium, hydroxyapatite, etc. These materials can be incorporated into the shell material or may be applied to the shell surface forming a second layer.

Material of the connection post can be composed of a variety of biocompatible materials including but not limited to; aluminum, stainless steel, gold, titanium, titanium alloy, or other less precious metals can be uses for the temporary post, ceramic, acrylic, porelian, lithium desilicate, zirconia and other crystalline structure. It is anticipated that this material can be composed of materials that are anti-microbial, bacterior static to retarrd the growth or colonization of the surface and internal surfaces with micro-organisms. Examples of such materials include but not limited to; silver, copper, magnesium, titanium, hydroxyapitite, etc.

The connection interface between the abutment shell is placed at the level the implant head platform. In the preferred embodiment there is a single interface at the implant plateform at the bone crest level. This interface is a mechanical connection to minimize the placement of a micro- or macro- connection gap within the tissue-zone. The preferred embodiment is screw-retained. It is anticipated that a cementable version of the immediate soft tissue implant preservation abutment shell can be fabricated.

The preferred embodiment of the shell is confined to the tissue-zone, but it is anticipated that a second design could include part of all of the tooth form that was extracted.

As shown in FIG. 8, the tooth-form temporary 70 that is selected or created to match the extracted tooth, is then luted to the outer perimeter 18 of shell 10 so that the patient leaves with a cosmetically equivalent tooth replacement to the one extracted.

Disposable Standard Cylindrical Implant Intra-operative Abutment: This component is used as intra-operative abutment that is placed during the immediate soft tissue implant preservation protocol to allowing bone grating materials to be placed within the bone gap between the implant surface and the bony residual socket. It also has the function to prevent bone grafting materials from entering into the internal screw hole of the implant prior to the placement of the immediate soft tissue implant preservation abutment. It is a single use, disposable component. It can be fabricated from a variety of materials and come in a variety of heights and widths. The preferred embodiment is an inexpensive polymer material allowing it to be screwed or press-fitted into place during the placement of the bone grafting materials.

Immediate soft tissue Abutment Texturing Bur: This component is a rotary bur that is designed to provide a microgeometric repetitive surface pattern forming a varying widths and varying depths ranging from 10 microns to about 50 microns. The irregular repetitive pattern is created using a chair-side rotary instrument on the surface of the immediate soft tissue implant preservation abutment to resurface the outer shell.

Some Improvements Over Prior Art:

Following are some improvements of the invention over known implant apparatuses and methods.

Preservation of the soft tissue architecture after the immediate removal of a tooth.

Ability to record the spatial relationship of the soft tissue residual gingival socket to the spatial position of the underlying root-form dental implant irrespective of the x, y, z axes relationship of these two independent structures. The non-concentric relationship is easily recorded and allows for the fabrication of a variety of prosthetic components to be used.

Provide a means to fabricate an immediate abutment or other prosthetic components using orientation markings and structural dimensions of the recording components. These components then enable the fabrication of dissimilar spatial positions to be recorded for custom fabrication of prosthetic components relationship soft tissue contours to the underlying root-from implant.

Support of the soft tissues to prevent collapse of bone and soft tissue during healing.

Creation a soft tissue "seal" of the replacement temporary to the overlying soft tissues. A soft tissue seal of the residual soft tissue socket of an extracted tooth in which an immediate implant has been placed.

Produce soft tissue adhesion by providing direct physically contact between the prosthesis and surrounding soft tissue socket.

Placement of a single interface between implant and prosthesis that is below the soft tissue proximal heights at or below the level of supporting bone.

One-piece prosthetic design that is a temporary that is screw retained.

Prosthesis emergence profile is over-contoured to provide an adequate soft tissue seal and soft tissue support to the soft tissues to preserve the natural architecture of the gingival tissues.

Prosthesis is under-contoured to provide an adequate soft tissue seal between prosthesis and soft tissue socket to support the soft tissues to preserve the natural architecture of the gingival tissues.

The supra-gingival contour of the tooth prosthesis is identical to the natural tooth while the sub-gingival possesses a emergence profile contour that is either over-contoured or under-contoured to compensate for the lack of ideal position of an implant in the vertical, horizontal, and buccal-lingual, mesial-distal angulations.

Anti-rotational prosthesis screw-retained temporary prosthesis. Anti-rotational features in the implant/abutment connection.

The temporary abutment is constructed directly chair-side utilizing a prefabricated series of anatomic shells who's central access is eccentric to allow either an over-contoured or under-contoured subgingival emergence profile thereby allowing adequate support of the soft tissue and ensuring a seal being formed between the soft tissue socket and the temporary prosthesis.

The temporary abutment is anticipated to prefabricate in a variety of sizes and elliptical shapes of the root surfaces. Different vertical heights will be provided. The shapes will be designed to represent replacement of an extracted tooth.

Antimicrobial Surface and/or material to be used.

Incorporation of a microtexture on the surface of the temporary that has a regular geometric configuration to encourage soft tissue connection.

Use of a specialized bur that creates a regular pattern on the surface of the temporary.

The following designs are anticipated, but not limited to:

Temporary transmucosal (root form) implant temporary shell root form in the soft tissue zone from the platform head of the implant to the free-gingival margin.

The superior 1-3 mm may be smooth surfaced to provide a plaque free zone.

Inferior surface (below the 1-3 mm plaque zone) may be textured to encourage soft tissue adhesion.

Surface treatment of the shell by steam cleaning.

The transmucosal temporary component of the invention makes the physical and structural connection between the dental implant and the overlying soft tissues for the final connection to a tooth replacement prosthesis visible inside the mouth.

The implant 30 and screw 50 are made of surgical steel or other metals such as titanium/titanium alloy. The post is made of steel, ceramic of other durable material such as gold alloy, e.g. AuPdAg (gold-palladium-silver). The shell is zirconium oxide ceramic or other suitable material as listed above. The luting compound is, for example resin or resin-ionomer. The tooth-form temporary 70 is made of material such as polymethyl methacrylate (PMMA), polyetheretherketone (PEEK), lithium disilicate, or zirconium dioxide.

While specific embodiments of the invention have been shown and described in detail to illustrate the application of the principles of the invention, it will be understood that the invention may be embodied otherwise without departing from such principles.

What is claimed is:

1. A soft tissue preservation, dental implant arrangement, comprising:
    a hollow shell with an interior volume and a shell axis, the hollow shell having an outer surface configured to engage a soft tissue socket after a tooth has been extracted from a bone socket, the shell having a first perimeter configured for placement toward the bone socket and a second perimeter configured for placement adjacent an outer surface of the soft tissue socket, the first perimeter being smaller than the second perimeter so that the shell tapers outwardly from the first perimeter to the second perimeter, the second perimeter having an asymmetrically scalloped shape including a distal peak, a mesial peak opposite the distal peak, a lingual valley between the distal peak and the mesial peak, and a facial valley between the distal peak and the mesial peak;
    a dental implant having an implant axis and being configured for placement in the bone socket; and
    a temporary post coupled to and coaxial with the dental implant, the temporary post extending in the interior volume of the hollow shell such that an interior space is formed between an outer surface of the post and an inner surface of the shell, a minimum dimension of the hollow shell being greater than a maximum dimension of the post such that no part of the shell contacts the post despite non-alignment of the shell axis and the implant axis, the interior space between the outer surface of the post and the inner surface of the shell being configured to receive a luting compound for coupling the outer surface of the post and the inner surface of the shell.

2. The arrangement of claim 1, wherein the lingual valley is at a different height above the first perimeter than the facial valley.

3. The arrangement of claim 1, further comprising the luting compound filling the interior space between the shell and the temporary post and setting solid for fixing the shell to the dental implant so that the post, the shell and the luting together form an abutment for the soft tissue socket, the hollow shell having an outer bio-compatible surface for engaging the soft tissue socket.

4. The arrangement of claim 1, wherein the post and the shell each include at least three spaced markings, the markings on the shell being on the inner surface of the shell and the markings on the post being on the outer surface of the post, the markings creating corresponding markings on an image of the post and shell when the post is connected to the implant and when the shell is in the soft tissue socket for recording data in the image corresponding to the relative position and angle between the shell and the post for use in creating at least one of an abutment or a crown for the soft tissue socket.

5. The arrangement of claim 1, wherein the distal and mesial peaks are not in a common plane with the shell axis.

6. The arrangement of claim 1, wherein the post and the shell each include at least three spaced markings, the markings on the shell being on the inner surface of the shell and the markings on the post being on the outer surface of the post, the markings creating corresponding markings on an image of the post and shell when the post is connected to the implant and when the shell is in the soft tissue socket for recording data in the image corresponding to the relative position and angle between the shell and the post for use in creating at least one of an abutment or a crown for the soft tissue socket, the markings on the shell include information about the size and shape of the shell and the markings on the post including information about the depth of the implant in the boney socket.

7. The arrangement of claim 1, wherein the post has an upper coronal portion for extending in the shell and a lower threaded portion for being treadably connected to the implant, at least part of the surface of the coronal portion being roughened and having at least one undercut, the post including at least one large diameter portion that is larger than the threaded portion for fixing the axial location of the post to the implant.

8. The arrangement of claim 1, wherein the post has an upper coronal portion for extending in the shell and a lower threaded portion for being treadably connected to the implant, the coronal portion having a breakaway portion and at least one large diameter portion that is larger than the threaded portion for fixing the axial location of the post to the implant.

9. The arrangement of claim 1, further comprising:
the luting compound filling the interior space between the shell and the temporary post and setting solid for fixing the shell to the dental implant so that the post, the shell and the luting compound together form an abutment for the soft tissue socket, and
a tooth-form temporary attached at the second perimeter for temporarily replacing an extracted tooth.

10. The arrangement of claim 1, wherein the shell is initially mechanically decoupled from the post and the dental implant such that the shell is freely movable and rotatable relative to the implant and the post while the dental implant is placed in the bone socket, the post is coupled to the dental implant, the shell is placed in the soft tissue socket with the post extending in the interior volume of the shell, and prior to the luting compound coupling the shell to the post.

11. The arrangement of claim 1, wherein the post includes a plurality of post markings and the shell includes a plurality of shell markings configured to indicate a relative position and orientation of the shell and the post.

12. The arrangement of claim 11, wherein the plurality of post markings and the plurality of shell markings include one or more indents, detents, laser etching, or colored markings.

13. The arrangement of claim 11, wherein the plurality of post markings and the plurality of shell markings are coded with an indication of at least one of a physical shape or a dimension of the shell.

14. The arrangement of claim 11, wherein the plurality of post markings and the plurality of shell markings are coded with an indication of at least one of a physical shape or a dimension of the post.

15. A soft tissue preservation, dental implant arrangement, comprising:
a hollow shell with an interior volume and a shell axis, the hollow shell having an outer surface for engaging a soft tissue socket that is left in gingival tissue immediately after a tooth has been extracted from a bone socket under the gingival tissue, the shell having a first perimeter adapted for placement toward the bone socket and a second perimeter adapted for placement adjacent an outer surface of the gingival tissue around the soft tissue socket, the first perimeter being smaller than the second perimeter so that the shell tapers outwardly from the first to the second perimeters, the second perimeter being asymmetrically scalloped with opposite distal and mesial peaks and opposite lingual and facial valleys between the peaks, and the shell being sized for closely engaging against the soft tissue socket without gaps;
a dental implant having an implant axis and being adapted for placement in the bone socket;
a temporary post rigidly connected to and coaxial with the dental implant, the temporary post extending in the interior volume of the hollow shell, a minimum inside diameter of the hollow shell being larger than a maximum outside diameter of the post and no part of the shell being in contact with any part of the post despite non-alignment of the shell axis with the implant axis and so the shell is at a first position and a first orientation as dictated by the soft tissue socket and has an independent position with respect to the post that is at a second orientation as dictated by the boney socket when the outer surface of the shell engages against the soft tissue socket without gaps and without requiring alignment of the shell axis to the implant axes and with freedom of relative position and angle between the shell and the post;
a luting compound filling the interior volume between the shell and the temporary post and setting solid for fixing the shell to the dental implant so that the post, the shell and the luting compound together form an abutment for the soft tissue socket, the hollow shell having an outer bio-compatible surface for engaging the soft tissue socket;
a screw extending in the post and connecting the post to the implant; and
a plug in the post above the screw and in the luting compound for providing access to the screw when the plug is removed for disconnecting the post from the implant.

16. The arrangement of claim 15, wherein the lingual valley is at a different height above the first perimeter than the facial valley.

17. The arrangement of claim 15, wherein the post includes at least three post markings and the shell includes at least three shell markings configured to indicate a relative position and orientation of the shell and the post.

18. The arrangement of claim 17, wherein the at least three post markings and the at least three shell markings include one or more indents, detents, laser etching, or colored markings.

19. The arrangement of claim 17, wherein the at least three post markings and the at least three shell markings are coded with an indication of at least one of a physical shape or a dimension of the shell, and the at least three post markings and the at least three shell markings are coded with an indication of at least one of a physical shape or a dimension of the post.

* * * * *